US012138434B2

(12) United States Patent
Ueda et al.

(10) Patent No.: US 12,138,434 B2
(45) Date of Patent: Nov. 12, 2024

(54) PUNCTURE NEEDLE AND CATHETER ASSEMBLY

(71) Applicant: TERUMO KABUSHIKI KAISHA, Tokyo (JP)

(72) Inventors: Takehiko Ueda, Kofu (JP); Masahiko Nagasawa, Kai (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1063 days.

(21) Appl. No.: 16/918,236

(22) Filed: Jul. 1, 2020

(65) Prior Publication Data

US 2020/0330014 A1   Oct. 22, 2020

Related U.S. Application Data

(63) Continuation of application No. PCT/JP2019/011189, filed on Mar. 18, 2019.

(30) Foreign Application Priority Data

| Mar. 19, 2018 | (JP) | 2018-051395 |
| Aug. 13, 2018 | (JP) | 2018-152450 |
| Oct. 31, 2018 | (JP) | 2018-206087 |

(51) Int. Cl.
*A61M 5/32* (2006.01)
*A61B 5/15* (2006.01)
*A61M 5/158* (2006.01)

(52) U.S. Cl.
CPC ..... *A61M 5/3286* (2013.01); *A61B 5/150106* (2013.01); *A61B 5/150167* (2013.01);

(Continued)

(58) Field of Classification Search
CPC ........ A61B 5/150458; A61B 5/150106; A61B 5/150167; A61B 5/150992; A61M 5/3286; A61M 5/158
See application file for complete search history.

(56) References Cited

U.S. PATENT DOCUMENTS

| 2,904,045 A | 9/1959 | Owings |
| 4,046,144 A * | 9/1977 | McFarlane ........ A61M 25/0693 |
| | | 604/168.01 |

(Continued)

FOREIGN PATENT DOCUMENTS

| CN | 2801183 Y | 8/2006 |
| DE | 10 2005 027 147 A1 | 12/2006 |

(Continued)

OTHER PUBLICATIONS

Extended European Search Report dated Oct. 26, 2020 in corresponding European Patent Application No. 19771077.5.

(Continued)

*Primary Examiner* — James D Ponton
(74) *Attorney, Agent, or Firm* — Foley & Lardner LLP

(57) ABSTRACT

A puncture needle for medical use includes: a main body that is rod-shaped and that comprises a distal end portion comprising a blade surface. The blade surface includes: a first blade surface portion that extends so as to incline with respect to a central axis of the main body, and a second blade surface portion that is formed on a back side of the first blade surface. A blade edge having a needle tip at one end is formed by a ridge line where the first blade surface portion meets the second blade surface portion. The first blade surface portion is constituted by a concave surface that is concave in a side view of the main body.

16 Claims, 21 Drawing Sheets

(52) U.S. Cl.
CPC .. *A61B 5/150458* (2013.01); *A61B 5/150992* (2013.01); *A61M 5/158* (2013.01)

(56) References Cited

U.S. PATENT DOCUMENTS

| | | | |
|---|---|---|---|
| 4,889,529 A * | 12/1989 | Haindl | A61M 5/158 604/274 |
| 5,618,272 A | 4/1997 | Nomura | |
| 5,733,266 A | 3/1998 | Gravlee | |
| 5,735,813 A | 4/1998 | Lewis | |
| 5,752,942 A | 5/1998 | Doyle et al. | |
| 5,797,961 A | 8/1998 | Smith et al. | |
| 5,817,074 A | 10/1998 | Racz | |
| 5,968,022 A | 10/1999 | Saito | |
| 5,976,115 A | 11/1999 | Parris et al. | |
| 6,120,517 A | 9/2000 | Daum et al. | |
| 6,171,280 B1 | 1/2001 | Imazu et al. | |
| 6,213,989 B1 | 4/2001 | Utterberg | |
| 6,517,523 B1 | 2/2003 | Kaneko et al. | |
| 6,554,760 B2 | 4/2003 | Lamoureux et al. | |
| 6,569,077 B2 | 5/2003 | Schmidt | |
| 6,607,503 B1 | 8/2003 | Berbers | |
| 6,626,887 B1 | 9/2003 | Wu | |
| 6,740,277 B2 | 5/2004 | Howell et al. | |
| 7,002,098 B2 | 2/2006 | Adams | |
| 7,252,653 B2 | 8/2007 | Ueda et al. | |
| 7,435,239 B2 | 10/2008 | Yatabe et al. | |
| 7,722,549 B2 | 5/2010 | Nakao | |
| 8,075,529 B2 | 12/2011 | Nakajima et al. | |
| 8,097,013 B2 | 1/2012 | Oki et al. | |
| 8,262,574 B2 | 9/2012 | Placek et al. | |
| 8,273,062 B2 | 9/2012 | Villette | |
| 8,328,772 B2 | 12/2012 | Kinast et al. | |
| 8,439,877 B2 | 5/2013 | Burkholz | |
| 8,545,454 B2 | 10/2013 | Kuracina et al. | |
| 8,545,478 B2 | 10/2013 | Gough et al. | |
| 9,610,067 B2 | 4/2017 | Sekikawa | |
| 9,622,719 B2 | 4/2017 | Maizes | |
| 9,662,477 B2 | 5/2017 | Yamada et al. | |
| 9,693,803 B2 | 7/2017 | Mamiya | |
| 9,700,304 B2 | 7/2017 | Koziczynski et al. | |
| 9,757,148 B2 | 9/2017 | Vanderstek et al. | |
| 9,757,201 B2 | 9/2017 | Hendriks et al. | |
| 9,763,692 B2 | 9/2017 | Bowe et al. | |
| 2001/0005178 A1 * | 6/2001 | Stewart | G06Q 10/109 340/8.1 |
| 2004/0138528 A1 | 7/2004 | Richter et al. | |
| 2007/0123935 A1 | 5/2007 | Myers | |
| 2008/0039796 A1 | 2/2008 | Nakajima | |
| 2008/0154217 A1 | 6/2008 | Carrez et al. | |
| 2009/0126636 A1 | 5/2009 | Correa et al. | |
| 2009/0254061 A1 | 10/2009 | Baron | |
| 2010/0030105 A1 | 2/2010 | Noishiki et al. | |
| 2010/0241150 A1 | 9/2010 | Oki et al. | |
| 2010/0305519 A1 | 12/2010 | McKinnon et al. | |
| 2011/0054406 A1 | 3/2011 | McKinnon | |
| 2011/0254202 A1 | 10/2011 | Aeschlimann | |
| 2014/0236024 A1 | 8/2014 | Bierhoff et al. | |
| 2014/0236104 A1 | 8/2014 | Haindl | |
| 2014/0242259 A1 | 8/2014 | Young | |
| 2014/0257190 A1 | 9/2014 | Yue et al. | |
| 2015/0223977 A1 | 8/2015 | Oberkircher et al. | |
| 2016/0175563 A1 | 6/2016 | Woehr et al. | |
| 2016/0183969 A1 | 6/2016 | Haselby et al. | |
| 2016/0235949 A1 | 8/2016 | Baid | |
| 2016/0310704 A1 | 10/2016 | Ng et al. | |
| 2016/0354066 A1 | 12/2016 | Asaoka et al. | |
| 2017/0043101 A1 | 2/2017 | Cole et al. | |
| 2017/0065334 A1 | 3/2017 | Wright et al. | |
| 2017/0119431 A1 | 5/2017 | Park et al. | |
| 2017/0119974 A1 | 5/2017 | Racz | |
| 2017/0216536 A1 * | 8/2017 | Scott | A61M 5/158 |
| 2017/0361070 A1 | 12/2017 | Hivert | |

FOREIGN PATENT DOCUMENTS

| | | |
|---|---|---|
| DE | 10 2012 204 166 A1 | 9/2012 |
| EP | 1 297 856 A1 | 4/2003 |
| EP | 1 610 697 A1 | 1/2006 |
| EP | 1 736 192 B1 | 3/2008 |
| EP | 1 996 090 A2 | 12/2008 |
| EP | 1 843 804 B1 | 5/2011 |
| EP | 2 437 842 A1 | 4/2012 |
| EP | 2 750 742 A1 | 7/2014 |
| EP | 2 181 725 B1 | 9/2014 |
| EP | 2 419 005 B1 | 11/2014 |
| EP | 2 809 398 A1 | 12/2014 |
| EP | 1 590 024 B1 | 4/2016 |
| EP | 2 200 684 B1 | 10/2016 |
| EP | 3 104 814 A1 | 12/2016 |
| EP | 3 237 052 A2 | 11/2017 |
| EP | 3 246 056 A1 | 11/2017 |
| EP | 3 260 050 A1 | 12/2017 |
| EP | 3 263 042 A1 | 1/2018 |
| EP | 3 297 709 A1 | 3/2018 |
| JP | H08-336593 A | 12/1996 |
| JP | H10-57490 A | 3/1998 |
| JP | 2000-262615 A | 9/2000 |
| JP | 2001-502191 A | 2/2001 |
| JP | 2001-293062 A | 10/2001 |
| JP | 2002-165881 A | 6/2002 |
| JP | 2003-102745 A | 4/2003 |
| JP | 2003-534037 A | 11/2003 |
| JP | 2004-057369 A | 2/2004 |
| JP | 2004-298278 A | 10/2004 |
| JP | 2005-095571 A | 4/2005 |
| JP | 3785069 B | 6/2006 |
| JP | 2007-135786 A | 6/2007 |
| JP | 2008-528222 A | 7/2008 |
| JP | 4145020 | 9/2008 |
| JP | 4388597 B | 12/2009 |
| JP | 4422791 B | 2/2010 |
| JP | 2010-167287 A | 8/2010 |
| JP | 4550757 B | 9/2010 |
| JP | 4573568 B | 11/2010 |
| JP | 2012-000239 A | 1/2012 |
| JP | 2012-030009 A | 2/2012 |
| JP | 2012-030010 A | 2/2012 |
| JP | 4884955 B | 2/2012 |
| JP | 4916113 | 4/2012 |
| JP | 2012-513320 A | 6/2012 |
| JP | 4950900 B | 6/2012 |
| JP | 4997456 B | 8/2012 |
| JP | 2012-528681 A | 11/2012 |
| JP | 3180120 U | 12/2012 |
| JP | 5148107 B | 2/2013 |
| JP | 2013-526940 A | 6/2013 |
| JP | 5232458 B | 7/2013 |
| JP | 5354827 B | 11/2013 |
| JP | 5365868 B | 12/2013 |
| JP | 2014-004249 A | 1/2014 |
| JP | 5436791 B | 3/2014 |
| JP | 2014-097415 A | 5/2014 |
| JP | 5538438 B | 7/2014 |
| JP | 2014-527446 A | 10/2014 |
| JP | 2014-533998 A | 12/2014 |
| JP | 5653655 B | 1/2015 |
| JP | 2015-123220 A | 7/2015 |
| JP | 2015-147042 A | 8/2015 |
| JP | 5781948 B | 9/2015 |
| JP | 2015-181671 A | 10/2015 |
| JP | 5870698 B | 3/2016 |
| JP | 2016-059427 A | 4/2016 |
| JP | 2016-064152 A | 4/2016 |
| JP | 5908198 B | 4/2016 |
| JP | 2016-067431 A | 5/2016 |
| JP | 2016-069678 A | 5/2016 |
| JP | 2016-096846 A | 5/2016 |
| JP | 2016-101179 A | 6/2016 |
| JP | 5937936 B | 6/2016 |
| JP | 5942060 B | 6/2016 |
| JP | 5945651 B | 7/2016 |
| JP | 5985129 B | 9/2016 |

(56) References Cited

FOREIGN PATENT DOCUMENTS

| | | |
|---|---|---|
| JP | 5985131 B | 9/2016 |
| JP | 6062643 B | 1/2017 |
| JP | 2017-505686 A | 2/2017 |
| JP | 2017-513622 A | 6/2017 |
| JP | 2017-131612 A | 8/2017 |
| JP | 3212548 U | 9/2017 |
| JP | 6198731 B | 9/2017 |
| JP | 2018-000844 A | 1/2018 |
| WO | WO-2004/045686 A1 | 6/2004 |
| WO | WO-2009/024522 A1 | 2/2009 |
| WO | WO-2014/136854 A1 | 9/2014 |
| WO | WO-2015/082566 A1 | 6/2015 |
| WO | WO-2016/047202 A1 | 3/2016 |
| WO | WO-2016/107922 A1 | 7/2016 |
| WO | WO-2016/199597 A1 | 12/2016 |
| WO | WO-2017/017934 A1 | 2/2017 |
| WO | WO-2017/017935 A1 | 2/2017 |
| WO | WO-2017/017936 A1 | 2/2017 |
| WO | WO-2017/026938 A1 | 2/2017 |

OTHER PUBLICATIONS

International Searching Authority, "Written Opinion," issued in connection with International Patent Application No. PCT/JP2019/011189, dated Apr. 16, 2019.

First Chinese Office Action on CN Appl. Ser. No. 201980020513.X dated Jan. 19, 2022 (14 pages).

Office Action issued in connection with European Appl. No. 19771077.5 dated Aug. 16, 2023.

International Searching Authority, "International Search Report," issued in connection with International Patent Application No. PCT/JP2019/011189, dated Apr. 16, 2019.

\* cited by examiner

CROSS SECTION ALONG I-I

CROSS SECTION ALONG II-II

CROSS SECTION ALONG III-III

CROSS SECTION ALONG IV-IV

CROSS SECTION ALONG V-V

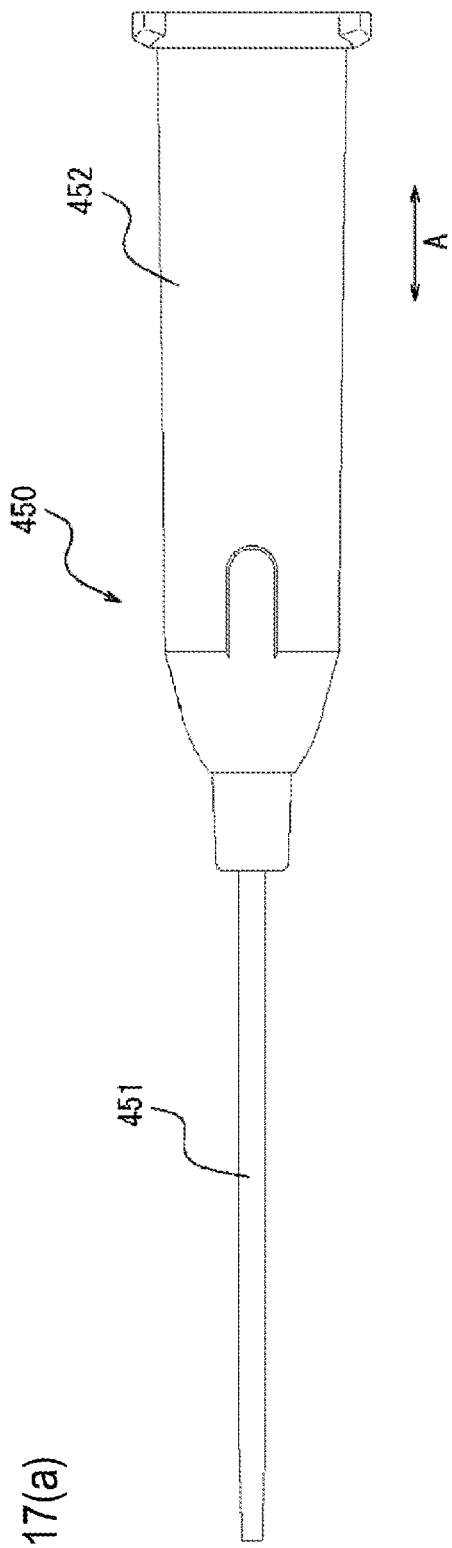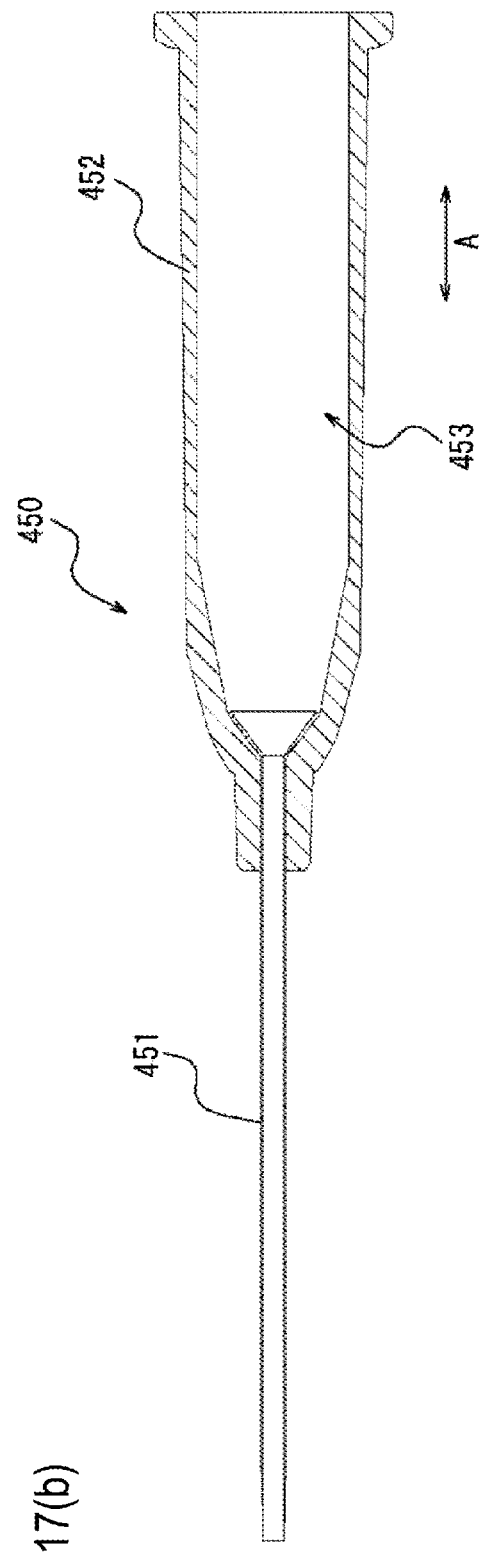
FIG. 17(a)
FIG. 17(b)

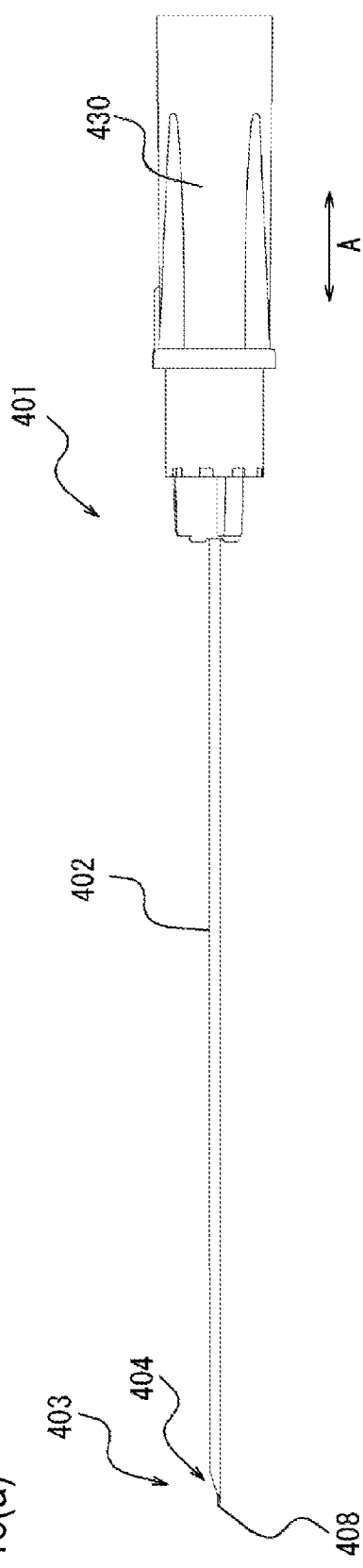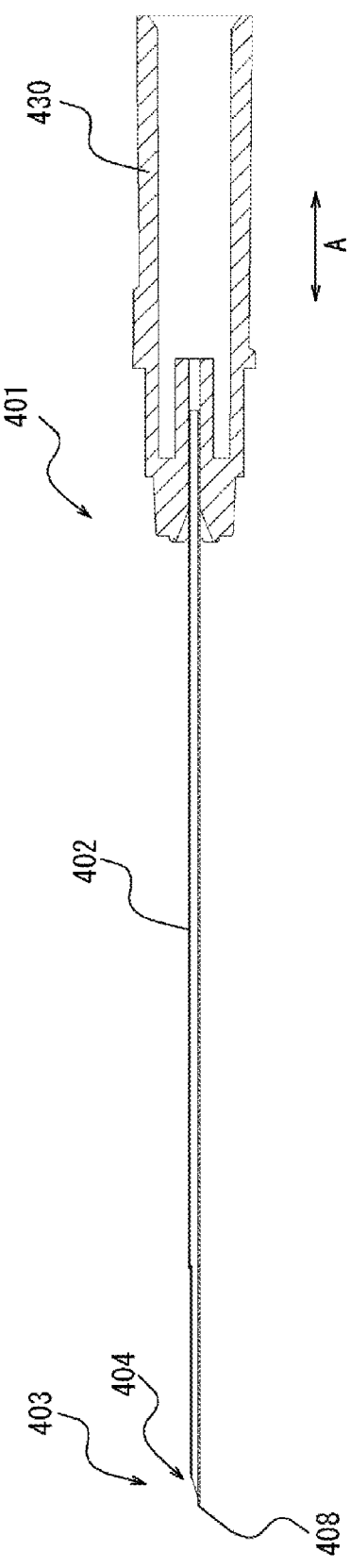
FIG. 18(a)
FIG. 18(b)

FIG. 21
FIG. 21(a)
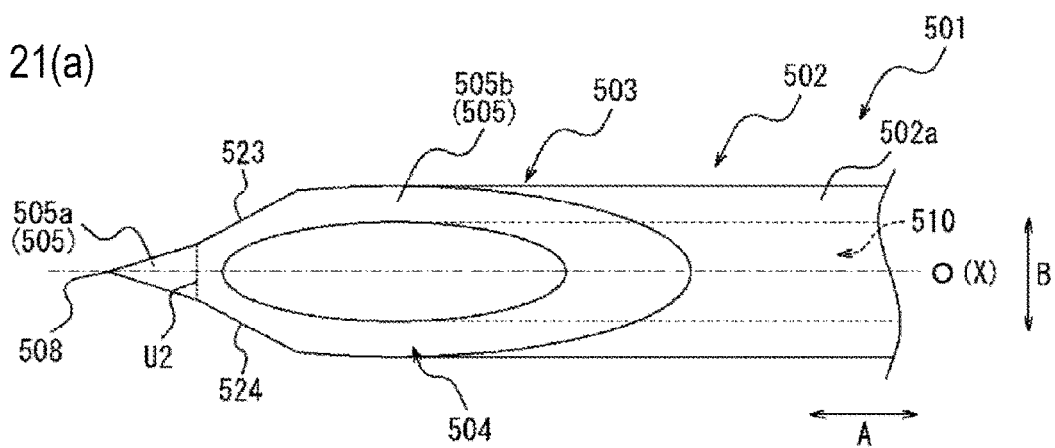
FIG. 21(b)
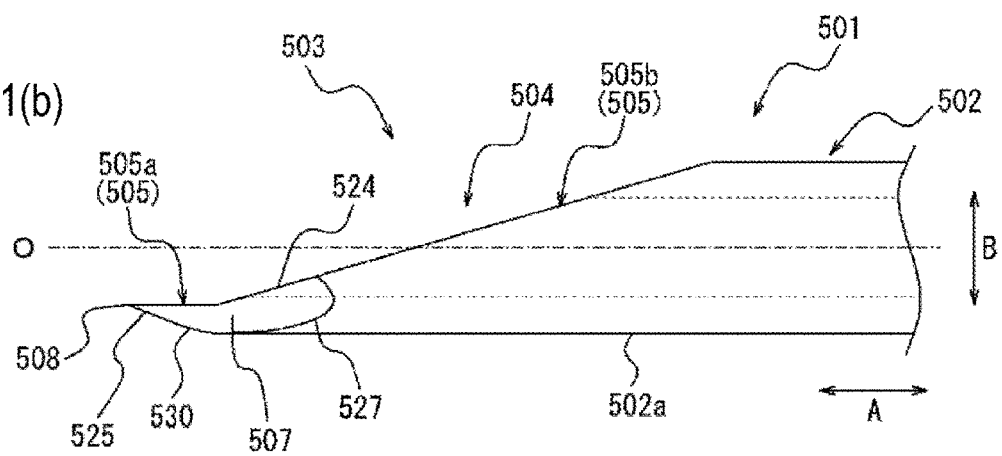
FIG. 21(c)
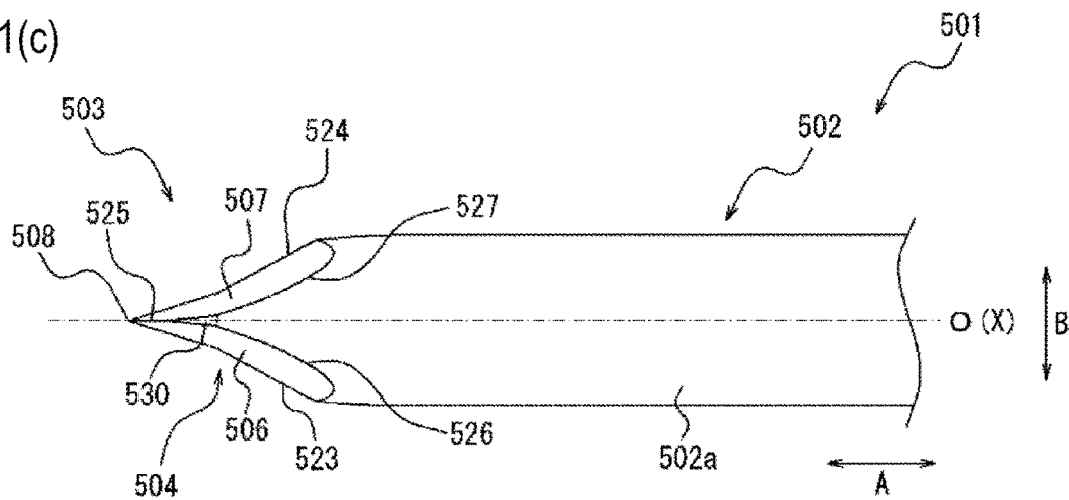

PUNCTURE NEEDLE AND CATHETER ASSEMBLY

CROSS-REFERENCE TO RELATED APPLICATIONS

This is a bypass continuation of PCT Application No. PCT/JP2019/011189, filed on Mar. 18, 2019, which claims priority to Japanese Application No. 2018-051395, filed on Mar. 19, 2018, Japanese Application No. 2018-152450, filed on Aug. 13, 2018, and Japanese Application No. 2018-206087, filed on Oct. 31, 2018. The contents of these applications are hereby incorporated by reference in their entireties.

BACKGROUND

The present disclosure relates to a puncture needle and a catheter assembly.

As a medical puncture needle such as a blood sampling needle or an indwelling needle for infusion, a conventionally known puncture needle has a distal end portion provided with a plurality of blade surfaces having different angles with respect to the longitudinal direction of the puncture needle in order to reduce pain when the puncture needle is inserted into a human body.

JP 2000-262615 A (U.S. Pat. No. 6,517,523) discloses an injection needle as the puncture needle described above. The injection needle disclosed in JP 2000-262615 A includes a taper-shaped tip portion formed by cutting a tip portion of a cylindrical main body obliquely from one side thereof, the taper-shaped tip portion of the needle being provided with: a first inclined surface connected to an outer periphery of the cylindrical main body and formed at a predetermined angle with respect to an axial direction (longitudinal direction) of the main body; a second inclined surface connected to the first inclined surface and formed at a larger angle than the predetermined angle of the first inclined surface with respect to the axial direction of the main body; and a third inclined surface connected to the second inclined surface, connected to a tip of a blade, and formed at a larger angle than the angle of the second inclined surface with respect to the axial direction of the main body.

JP 10-57490 A (U.S. Pat. No. 5,752,942) also discloses a hypodermic injection needle as a puncture needle. The hypodermic injection needle disclosed in JP 10-57490 A has a multi-beveled point, the multi-beveled point having a primary bevel, a pair of middle bevels, and a pair of tip bevels.

SUMMARY

When an injection needle has a distal end portion provided with a blade surface formed by connecting a plurality of surfaces having different angles with respect to the longitudinal direction, like the injection needles disclosed in JP 2000-262615 A and JP 10-57490 A, puncture resistance due to a ridge line (junction) formed on the boundary between surfaces can be reduced, whereby pain during puncture of the injection needle into a human body can be alleviated.

Meanwhile, regarding a puncture needle that is inserted into a vessel such as a blood vessel, it is common to use a puncture needle having a shorter length of a blade surface (hereinafter referred to as a "blade surface length") in a central axis direction in order to allow the entire blade surface to be easily inserted into the vessel. In such a puncture needle having a shorter blade surface length, even if the blade surface is constituted by multiple surfaces having different angles with respect to the central axis direction, the angle of the blade tip of the blade surface (hereinafter referred to as a "blade tip angle") in a side view cannot be reduced, and the blade tip angle tends to be relatively large. Therefore, such a puncture needle has a problem that the puncture resistance of the blade tip is increased, which makes it difficult to alleviate pain during piercing of the blade tip. In addition, when the puncture resistance of the blade tip is large, the blade tip cannot smoothly puncture a vessel wall such as a blood vessel wall during puncture into the vessel, and the vessel may avoid puncture by being pushed by the blade tip.

In view of the above, an object of the present disclosure is to provide a puncture needle having a blade surface shape capable of reducing a blade tip angle regardless of a blade surface length, and a catheter assembly including the puncture needle.

A puncture needle according to a first aspect of the present invention is a puncture needle for medical use provided with a blade surface formed on a distal end portion of a main body that is rod-shaped, wherein: the blade surface includes a first blade surface portion that extends so as to incline with respect to a central axis of the main body, and a second blade surface portion that is formed on a back side of the first blade surface portion and that forms a blade edge having a needle tip as one end by a ridge line where the second blade surface portion meets the first blade surface portion; and the first blade surface portion is constituted by a concave surface that is concave in a side view of the main body in which the first blade surface portion appears linear.

According to one embodiment of the present invention, the concave surface constituting the first blade surface portion includes a concave curved surface.

According to one embodiment of the present invention, the concave surface constituting the first blade surface portion includes a flat surface.

According to one embodiment of the present invention, the blade edge forms a concave shape in a front view of the main body as seen from a first blade surface portion side.

According to one embodiment of the present invention, the second blade surface portion extends to a proximal side beyond a midpoint of a blade surface region where the blade surface is formed in a central axis direction parallel to the central axis.

According to one embodiment of the present invention, in the side view, a tangent line of the first blade surface portion at a position of the needle tip extends substantially parallel to the central axis of the main body.

A puncture needle according to a second aspect of the present invention is a puncture needle for medical use provided with a blade surface formed on a distal end portion of a main body that is rod-shaped, wherein: the blade surface includes a first blade surface portion that extends so as to incline with respect to a central axis of the main body, and a second blade surface portion that is formed on the back side of the first blade surface portion and that forms a blade edge having a needle tip as one end by a ridge line where the second blade surface portion meets the first blade surface portion; and a tangent line of the first blade surface portion at a point where the first blade surface portion intersects with the central axis of the main body intersects with the second blade surface portion in a side view of the main body in which the first blade surface portion appears linear.

According to one embodiment of the present invention, the concave surface constituting the first blade surface portion includes a concave curved surface.

According to one embodiment of the present invention, the concave surface constituting the first blade surface portion includes a flat surface.

According to one embodiment of the present invention, the blade edge forms a concave shape in a front view of the main body as seen from a first blade surface portion side.

According to one embodiment of the present invention, the second blade surface portion extends to a proximal side beyond a midpoint of a blade surface region where the blade surface is formed in a central axis direction parallel to the central axis.

According to one embodiment of the present invention, in the side view, a tangent line of the first blade surface portion at a position of the needle tip extends substantially parallel to the central axis of the main body.

According to one embodiment of the present invention, a blade tip angle is from 12 degrees to 42 degrees, and a sectional angle is from 50 degrees to 110 degrees.

According to one embodiment of the present invention, a blade tip angle is from 15 degrees to 40 degrees, and a sectional angle is from 60 degrees to 85 degrees.

A puncture needle according to a third aspect of the present invention is a puncture needle for medial use provided with a blade surface at a distal end portion of a main body that has a hollow portion, wherein: the blade surface includes a first blade surface portion that extends so as to incline with respect to a central axis of the main body and that has an inner edge defining a distal-end opening of the hollow portion, and a second blade surface portion and a third blade surface portion that are formed on a distal side of the blade surface; the first blade surface portion is constituted by a concave surface that is concave in a side view of the main body in which the first blade surface portion appears linear, and includes a first blade edge formed by a ridge line where the first blade surface portion meets the second blade surface portion, and a second blade edge formed by a ridge line where the first blade surface portion meets the third blade surface portion; in a distal-end view when the main body is viewed from a distal side in a central axis direction, the first blade edge curves in a concave shape in a radial direction of the main body and extends to a needle tip, and a distance between the first blade edge and the inner edge of the first blade surface portion gradually decreases from a proximal end of the first blade edge toward the needle tip; and in the distal-end view, the second blade edge curves in a concave shape in the radial direction and extends to the needle tip, and a distance between the second blade edge and the inner edge of the first blade surface portion gradually decreases from a proximal end of the second blade edge toward the needle tip.

A puncture needle according to a fourth aspect of the present invention is a puncture needle for medical use provided with a blade surface formed on a distal end portion of a main body, wherein: the blade surface includes a first blade surface portion having at least a region that extends so as to incline with respect to a central axis of the main body, and a second blade surface portion that is formed on a back side of the first blade surface portion and that forms a blade edge having a needle tip as one end by a ridge line where the second blade surface portion meets the first blade surface portion; the blade edge has a distal-side blade edge that is straight and a proximal-side blade edge that is straight and located proximal to the distal-side blade edge; and in a front view when the main body is viewed from a first blade surface portion side, the distal-side blade edge and the proximal-side blade edge form a concave shape.

According to one embodiment of the present invention, the distal-side blade edge and the proximal-side blade edge form an obtuse angle in a side view of the main body in which the first blade surface portion appears linear.

According to one embodiment of the present invention, the distal-side blade edge is parallel to the central axis of the main body in a side view of the main body in which the first blade surface portion appears linear.

A puncture needle according to a fifth aspect of the present invention is a puncture needle for medical use provided with a blade surface formed on a distal end portion of a main body, wherein: the blade surface includes a first blade surface portion having at least a region that extends so as to incline with respect to a central axis of the main body, and a second blade surface portion that is formed on a back side of the first blade surface portion and that forms a blade edge having a needle tip as one end by a ridge line where the second blade surface portion meets the first blade surface portion; the first blade surface portion includes a distal-side blade surface portion that is flat and that includes the needle tip, and a proximal-side blade surface portion that is flat, is inclined more than the distal-side blade surface portion with respect to the central axis, and is located proximal to the distal-side blade surface portion; and the second blade surface portion extends across both a back side of the distal-side blade surface portion and a back side of the proximal-side blade surface portion.

According to one embodiment of the present invention, the blade edge has a distal-side blade edge that is straight and is formed by a ridge line where the distal-side blade surface portion of the first blade surface portion meets the second blade surface portion, and a proximal-side blade edge that is straight and is formed by a ridge line where the proximal-side blade surface portion of the first blade surface portion meets the second blade surface portion, and the distal-side blade edge and the proximal-side blade edge form a concave shape in a front view when the main body is viewed from a first blade surface portion side.

According to one embodiment of the present invention, the distal-side blade surface portion is parallel to the central axis of the main body in a side view of the main body in which the first blade surface portion appears linear.

According to one embodiment of the present invention, the distal-side blade surface portion and the proximal-side blade surface portion form an obtuse angle in a side view of the main body in which the first blade surface portion appears linear.

According to one embodiment of the present invention, the puncture needle includes, supposing that the blade edge is defined as a first blade edge, a third blade surface portion that is formed on a back side of the first blade surface portion and that forms a second blade edge having the needle tip as one end by a ridge line where the third blade surface portion meets the first blade surface portion, wherein: the second blade surface portion and the third blade surface portion form a third blade edge having the needle tip as one end by a ridge line where the second blade surface portion meets the third blade surface portion on the back side of the first blade surface portion; and a transition portion is formed on a proximal side of the third blade edge and on a distal side of an outer peripheral surface of the main body.

A puncture needle according to a sixth aspect of the present invention is a puncture needle for medical use provided with a blade surface formed on a distal end portion of a main body, wherein: the blade surface includes a first blade surface portion having at least a region that extends so as to incline with respect to a central axis of the main body, and a second blade surface portion that is formed on a back side of the first blade surface portion and that forms a blade edge having a needle tip as one end by a ridge line where the second blade surface portion meets the first blade surface portion; the first blade surface portion includes a distal-side blade surface portion that is flat and that includes the needle tip, and a proximal-side blade surface portion that is flat, is inclined more than the distal-side blade surface portion with respect to the central axis, and is located proximal to the distal-side blade surface portion; the blade edge has a distal-side blade edge that is straight and is formed by a ridge line where the distal-side blade surface portion of the first blade surface portion meets the second blade surface portion, and a proximal-side blade edge that is straight and is formed by a ridge line where the proximal-side blade surface portion of the first blade surface portion meets the second blade surface portion; and the distal-side blade edge and the proximal-side blade edge form a concave shape in a front view when the main body is viewed from a first blade surface portion side.

According to one embodiment of the present invention, the puncture needle includes, supposing that the blade edge is defined as a first blade edge, a third blade surface portion that is formed on a back side of the first blade surface portion and that forms a second blade edge having the needle tip as one end by a ridge line where the third blade surface portion meets the first blade surface portion, wherein the second blade surface portion and the third blade surface portion form a third blade edge having the needle tip as one end by a ridge line where the second blade surface portion meets the third blade surface portion on the back side of the first blade surface portion, and a curved transition portion formed on a proximal side of the third blade edge and on a distal side of an outer peripheral surface of the main body.

A catheter assembly according to a seventh aspect of the present invention includes: the puncture needle described above; a catheter into which the puncture needle is inserted; and a catheter hub holding the catheter.

The present disclosure can provide: a puncture needle having a blade surface shape capable of reducing a blade tip angle, regardless of a blade surface length; and a catheter assembly provided with the puncture needle.

BRIEF DESCRIPTION OF THE DRAWINGS

FIGS. 17(a) and 17(b) are an external view and a sectional view, respectively, of an outer tube member including a catheter in the catheter assembly shown in FIG. 16.

FIGS. 18(a) and 18(b) are an external view and a sectional view, respectively, of a puncture needle, as one embodiment, in the catheter assembly shown in FIG. 16.

FIGS. 21(a), 21(b), and 21(c) are a front view, a side view, and a rear view of a main body of a puncture needle as one embodiment, respectively.

DESCRIPTION OF EMBODIMENTS

Figure 1A:
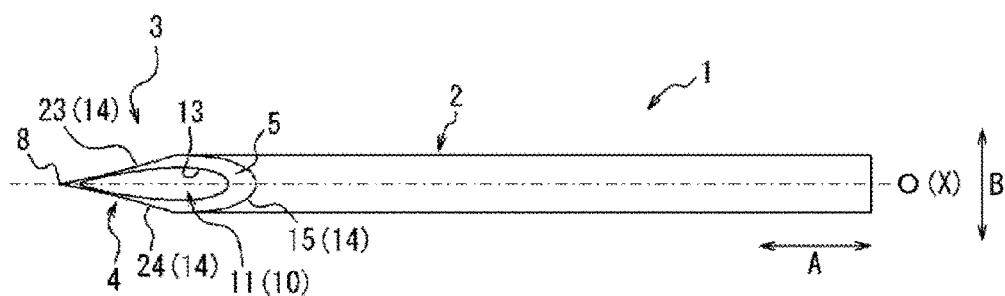
FIGS. 1(a), 1(b), 1(c), and 1(d) are a front view, a side view, a rear view, and a perspective view of a main body of a puncture needle as one embodiment, respectively.

Hereinafter, embodiments of a medical puncture needle and a catheter assembly according to the present disclosure will be described with reference to FIGS. 1 to 22. In the drawings, same members and parts are denoted by the same reference numerals.

First Embodiment

FIG. 1 is a view showing a main body 2 of a puncture needle 1 as one embodiment. Specifically, FIG. 1(a) is a front view of the main body 2 of the puncture needle 1, FIG. 1(b) is a side view of the main body 2 of the puncture needle 1, and FIG. 1(c) is a rear view of the main body 2 of the puncture needle 1. FIG. 1(d) is a perspective view of the main body 2 of the puncture needle 1. Further, FIG. 2(a) is an enlarged front view of a part of the main body 2 of the puncture needle 1 shown in FIG. 1(a). FIG. 2(b) is an enlarged side view of a part of the main body 2 of the puncture needle 1 shown in FIG. 1(b).

As shown in FIGS. 1(a) to 1(d), 2(a), and 2(b), the puncture needle 1 has the rod-shaped main body 2, and a blade surface 4 is formed on a distal end portion 3 of the main body 2. Specifically, the main body 2 in the present embodiment is a tubular body, and defines a hollow portion 10 extending in a central axis direction A parallel to a central axis O of the main body 2.

More specifically, the main body 2 in the present embodiment is a tubular body in which a cross section perpendicular to the central axis direction A has a substantially circular outer shape.

As shown in FIGS. 1(a) to 1(d), 2(a) and 2(b), the blade surface 4 is constituted by a plurality of blade surface portions. Specifically, the blade surface 4 in the present embodiment includes a first blade surface portion 5 as a front blade surface, and a second blade surface portion 6 and a third blade surface portion 7 as back blade surfaces. In other words, the main body 2 of the puncture needle 1 according to the present embodiment includes the blade surface 4 that is back cut.

The first blade surface portion 5 is inclined with respect to the central axis O of the main body 2 and extends to a needle tip 8. The "needle tip" means the tip of the puncture needle 1 in the central axis direction A, that is, the tip of the main body 2, and also means a blade tip, which is the tip of the blade surface 4. Therefore, in the following description, the "distal side" means the needle tip side in the central axis direction A of the puncture needle 1, and the "proximal side" means the side opposite to the needle tip side in the central axis direction A of the puncture needle 1.

The second blade surface portion 6 and the third blade surface portion 7 are formed on the back side of the first blade surface portion 5. The second blade surface portion 6 forms a blade edge 23 having the needle tip 8 as one end by a ridge line where the second blade surface portion 6 meets the first blade surface portion 5. The third blade surface portion 7 forms a blade edge 24 having the needle tip 8 as one end by a ridge line where the third blade surface portion 7 meets the first blade surface portion 5. The second blade surface portion 6 and the third blade surface portion 7 form a blade edge 25 having the needle tip 8 as one end at the back side of the first blade surface portion 5 by a ridge line where they meet each other.

Hereinafter, for convenience of description, the blade edge 23 formed by the ridge line where the first blade surface portion 5 and the second blade surface portion 6 meet is referred to as a "first blade edge 23". Further, for convenience of description, the blade edge 24 formed by the ridge line where the first blade surface portion 5 and the third blade surface portion 7 meet is referred to as a "second blade edge 24". Furthermore, for convenience of description, the blade edge 25 formed by the ridge line where the second blade surface portion 6 and the third blade surface portion 7 meet is referred to as a "third blade edge 25". When the puncture needle 1 punctures the surface of a living body, the first blade edge 23, the second blade edge 24, and the third blade edge 25 function as cutting edges for cutting the skin and reduce puncture resistance.

Further, a blade edge formed by a ridge line where the second blade surface portion 6 meets the outer peripheral surface of the main body 2 is referred to as a "fourth blade edge 26". Moreover, a blade edge formed by a ridge line where the third blade surface portion 7 meets the outer peripheral surface of the main body 2 is referred to as a "fifth blade edge 27".

As the material of the main body 2 in the present embodiment, a metal material such as stainless steel, aluminum or an aluminum alloy, titanium or a titanium alloy, etc. can be used.

Further, the main body 2 in the present embodiment is a tubular body in which the inner diameter of the inner peripheral surface and the outer diameter of the outer peripheral surface are uniform in the central axis direction A, and the proximal end in the central axis direction A is connected to a medical device such as a syringe via a needle hub or the like. Therefore, the puncture needle 1 may have a needle hub or the like connected to the main body 2.

Although, in the main body 2 in the present embodiment, the inner peripheral surface defines the hollow portion 10, and the inner diameter of the inner peripheral surface and the outer diameter of the outer peripheral surface are uniform in the central axis direction A, the configuration is not limited thereto. For example, the inner diameter of the inner peripheral surface and the outer diameter of the outer peripheral surface of the main body 2 may gradually decrease toward the distal side in the central axis direction A. Further, for example, the outer diameter of the main body 2 may be tapered so as to gradually decrease toward the distal side in the central axis direction A, and the inner diameter of the main body 2 may be uniform in the central axis direction A. Furthermore, the main body 2 may have, in a part thereof in the central axis direction A, a region where the inner diameter gradually decreases or gradually increases toward the distal side in the central axis direction A. That is, regarding the inner diameter and the outer diameter, the main body 2 may have various configurations according to a use or the like of the puncture needle 1.

In the present embodiment, the outer diameter of the main body 2 of the puncture needle 1 is uniform in the central axis direction A, and when viewed in a cross section including the entire central axis O, the outer peripheral surface of the main body 2 extends in the central axis direction A. Therefore, if the first blade surface portion 5 is inclined with respect to the central axis direction A, the inclination angle of the first blade surface portion 5 is larger than the inclination angle of the outer peripheral surface of the main body 2. However, when the main body of the puncture needle is configured such that the outer diameter gradually decreases or increases toward the distal side in the central axis direction A, the first blade surface portion is not only inclined with respect to the central axis direction A but also inclined with respect to the outer peripheral surface of the main body 2 in a cross section including the entire central axis O.

Each portion of the blade surface 4 of the main body 2 will be described below in detail.

[First Blade Surface Portion 5]

The first blade surface portion 5 has a symmetrical shape with respect to a virtual plane passing through the needle tip 8 and including the central axis O. Further, the first blade surface portion 5 linearly extends substantially perpendicular to the virtual plane at an arbitrary cross section perpendicular to the central axis direction A at the position of the first blade surface portion 5. The details will be described later with reference to FIGS. 4(a) to 4(e). In other words, the first blade surface portion 5 appears linear when viewed from a direction perpendicular to the virtual plane, that is, in a side view (see FIGS. 1(b) and 2(b)). Hereinafter, for convenience of description, the virtual plane passing through the needle tip 8 and including the central axis O is simply referred to as a "central plane X". Further, a side view (see FIGS. 1(b) and 2(b)) of the main body 2 in which the first blade surface portion 5 appears linear may be simply referred to as a "side view".

Figure 1B:
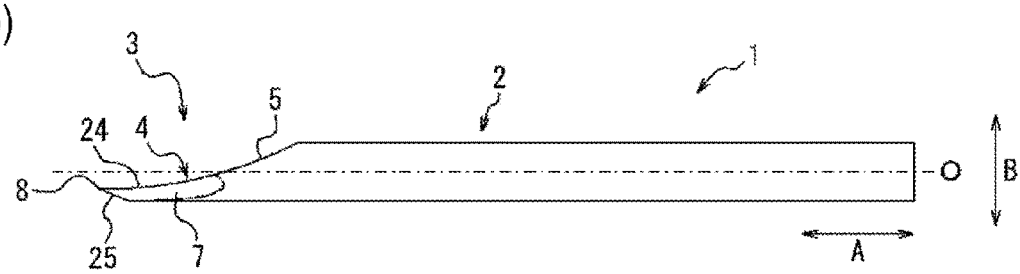
Figure 1C:
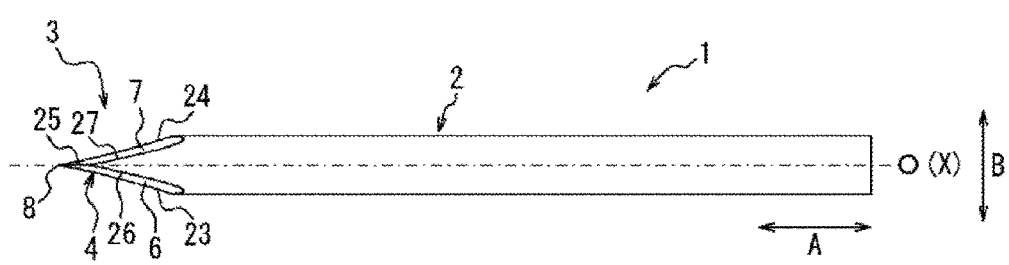
Figure 1D:
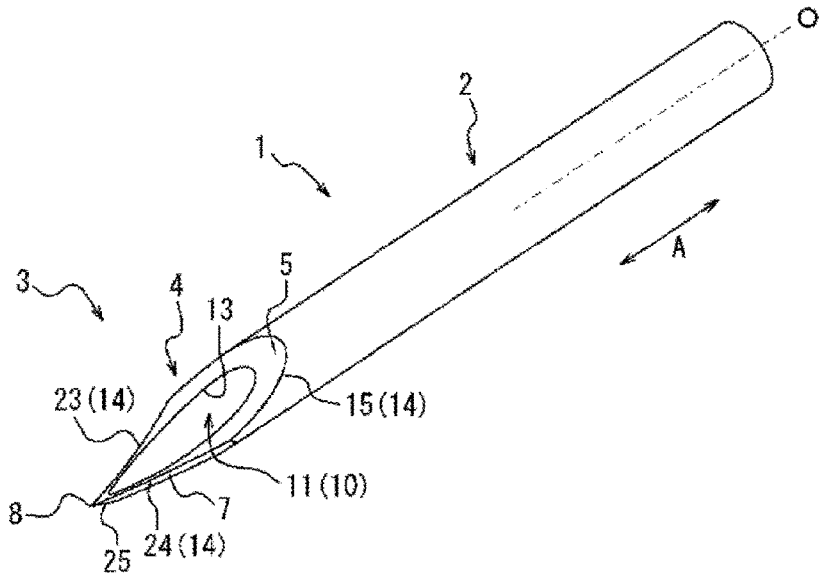
Figures 2A, 2B:
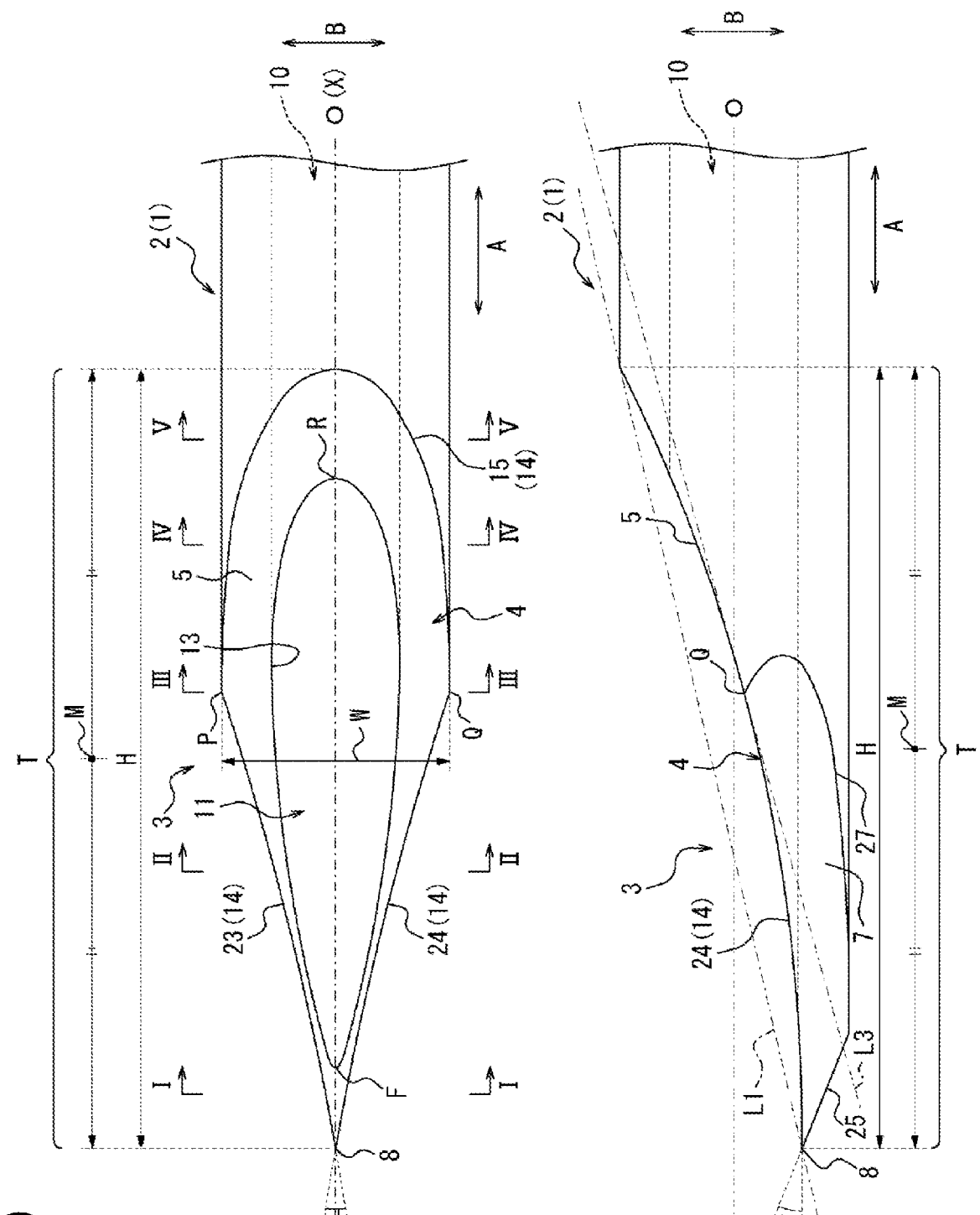
FIGS. 2(a) and 2(b) are enlarged views showing the vicinity of a distal end portion of the main body of the puncture needle shown in FIGS. 1(a) and 1(b), respectively.

The first blade surface portion 5 is constituted by a concave surface that is concave in the side view (see FIGS. 1(b) and 2(b)). The "concave surface" is not limited to a single curved surface having a concave shape, and is not particularly limited, as long as it is a concave surface in the side view (see FIGS. 1(b) and 2(b)) of the main body 2 in which the first blade surface portion 5 appears linear. For example, the concave surface may be constituted by a plurality of continuous flat surfaces.

Due to the configuration in which the first blade surface portion 5 is constituted by the abovementioned concave surface, an angle of a tangent line L2 of the first blade surface portion 5 with respect to the central axis direction A at the position of the needle tip 8 can be deceased in the side view (see FIG. 2(b)), as compared with a case where the first blade surface portion 5 is constituted by a single flat surface represented by a straight line L1 passing through the proximal end of the first blade surface portion 5 and the needle tip 8 in the side view (see FIG. 2(b)). Therefore, according to the configuration in which the first blade surface portion 5 is constituted by the abovementioned concave surface, the puncture needle 1 having a small blade tip angle α is easily achieved. The "blade tip angle α" here means an angle at the needle tip 8 in the side view (see FIG. 2(b)). More specifically, the blade tip angle α in the present embodiment indicates an angle formed by an intersection at the needle tip 8 between the tangent line L2 of the first blade surface portion 5 at the position of the needle tip 8 and the third blade edge 25 formed on the back side of the first blade surface portion 5 in the side view (see FIG. 2(b)).

In other words, the puncture needle 1 can be configured such that, even when the inclination angle of the first blade surface portion 5 with respect to the central axis O is increased in order to reduce the blade surface length H, the blade tip angle α does not increase accordingly. That is, the puncture needle 1 can be easily configured such that both the blade surface length H and the blade tip angle α are reduced. The "blade surface length H" means the length of the blade surface in the central axis direction A (see FIG. 2(a)).

Therefore, for example, the blade tip angle α can be set to be substantially equal to or less than that of a so-called "regular bevel" (a puncture needle in which an inclination angle of a first blade surface portion with respect to the central axis direction A when the first blade surface portion is constituted by a flat surface is 12 degrees) mainly used for intramuscular injection or the like, while setting the blade surface length H in the central axis direction A to be shorter than the blade surface length of the "regular bevel" and to be substantially equal to the blade surface length of a so-called "short bevel" (a puncture needle in which an inclination angle of a first blade surface portion with respect to the central axis direction A when the first blade surface portion is constituted by a flat surface is 18 degrees) mainly used for intravenous injection or the like. That is, it is possible to achieve the puncture needle 1 that can reduce puncture resistance on the blade surface 4 and can be easily and reliably inserted into a vessel, with a short blade surface length H by which the puncture needle 1 is unlikely to pierce through a vessel such as a vein. Further, since the puncture resistance in the vicinity of the needle tip 8 can be reduced, an amount of change in the puncture resistance can be reduced, and an amount of change in force applied by a medical worker in the puncture direction during puncture can also be reduced. Therefore, it is possible to achieve the puncture needle 1 that is easily operated by a medical worker when puncturing.

Further, it is preferable that, in the side view (see FIG. 2(b)), the blade tip angle α is set to 15 degrees to 27 degrees, while keeping an angle of the straight line L1 passing through the proximal end of the first blade surface portion 5 and the needle tip 8 with respect to the central axis O within the range of 13 degrees or more and 20 degrees or less. If the blade tip angle α is less than 15 degrees, the blade tip becomes too thin, so that predetermined performance may not be able to be satisfied due to damage or the like during a manufacturing process. Thus, the manufacture of such a blade tip is difficult. Even if it can be manufactured, the strength may be insufficient. If the angle exceeds 27 degrees, the blade tip angle becomes equal to the blade tip angle α of the so-called short bevel, so that the puncture resistance during puncture increases.

In the present embodiment, the tangent line L2 of the first blade surface portion 5 at the position of the needle tip 8 extends substantially parallel to the central axis O of the main body 2 in the side view (see FIG. 2(b), etc.). More specifically, in the side view (see FIG. 2(b), etc.), the tangent line L2 of the first blade surface portion 5 at the position of the needle tip 8 is not limited to be parallel to the central axis O of the main body 2 (the angle between the tangent line L2 and the central axis O is 0 degrees), but may be angled with respect to the central axis O of the main body 2 at an angle equal to or less than a predetermined angle (for example, 10 degrees). However, from the viewpoint of reducing the blade tip angle α, it is preferable that the tangent line L2 is parallel to the central axis O of the main body 2 at the position of the needle tip 8 of the first blade surface portion 5 in the side view (see FIG. 2(b), etc.).

In other words, it is preferable that, in the side view (see FIG. 2(b), etc.), the blade tip angle α is set to a predetermined angle (for example, 15 degrees) or more in order to prevent the blade tip from being excessively thin, while the tangent line L2 is set substantially parallel to the central axis O of the main body 2 at the position of the needle tip 8 of the first blade surface portion 5. That is, in the side view (see FIG. 2(b), etc.), an angle δ (equal to the blade tip angle α in the present embodiment) formed by the third blade edge 25 and the central axis O is greater than the angle (not shown in the present embodiment because it is 0 degrees) formed by the tangent line L2 and the central axis O at the position of the needle tip 8 of the first blade surface portion 5. With this configuration, the blade tip having smaller blade tip angle α and satisfying predetermined strength can be achieved.

Figure 5:
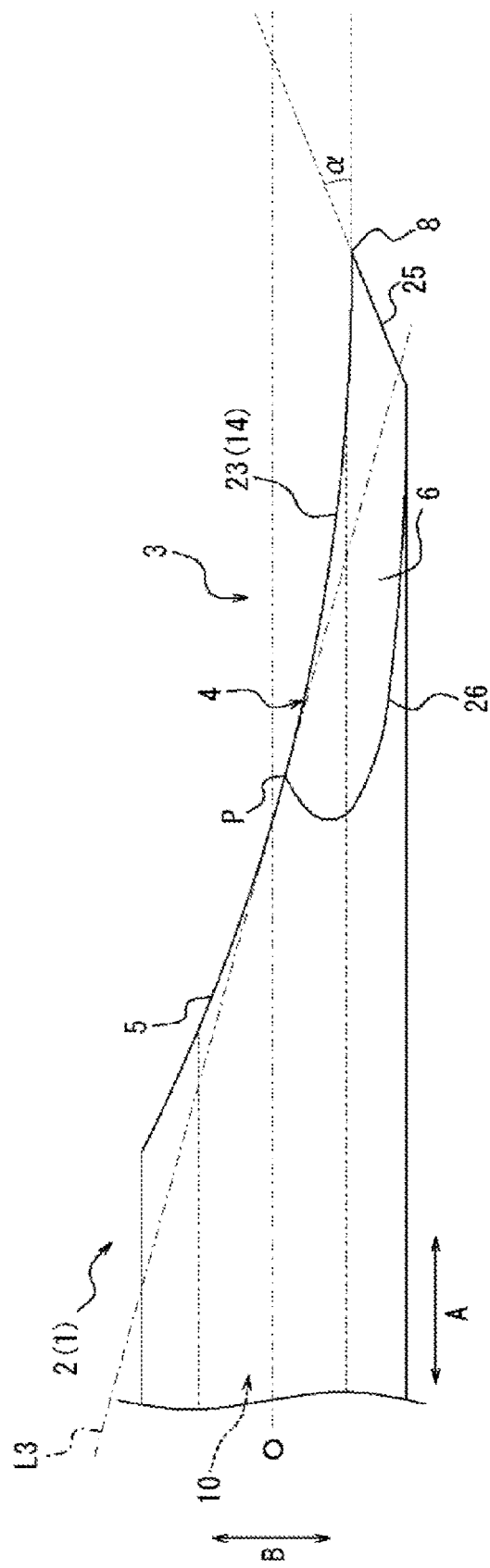
FIG. 5 is a side view as seen from a second blade surface portion side opposite to the side shown in FIG. 2(b).

Further, in the side view (see FIG. 2(b), etc.), a tangent line L3 of the first blade surface portion 5 at a point where the first blade surface portion 5 and the central axis O of the main body 2 intersect with each other intersects with the second blade surface portion 6 and the third blade surface portion 7. In FIG. 2(b), which shows the puncture needle 1 when viewed from the third blade surface portion 7 side, the tangent line L3 intersects with the third blade surface portion 7. On the other hand, FIG. 5 is a side view when viewed from the second blade surface portion 6 side opposite to the side shown in FIG. 2(b). In the side view shown in FIG. 5, the tangent line L3 intersects with the second blade surface portion 6. As described above, the tangent line L3 intersects with one of the second blade surface portion 6 and the third blade surface portion 7 in both side views shown in FIGS. 2(b) and 5.

Figure 3:
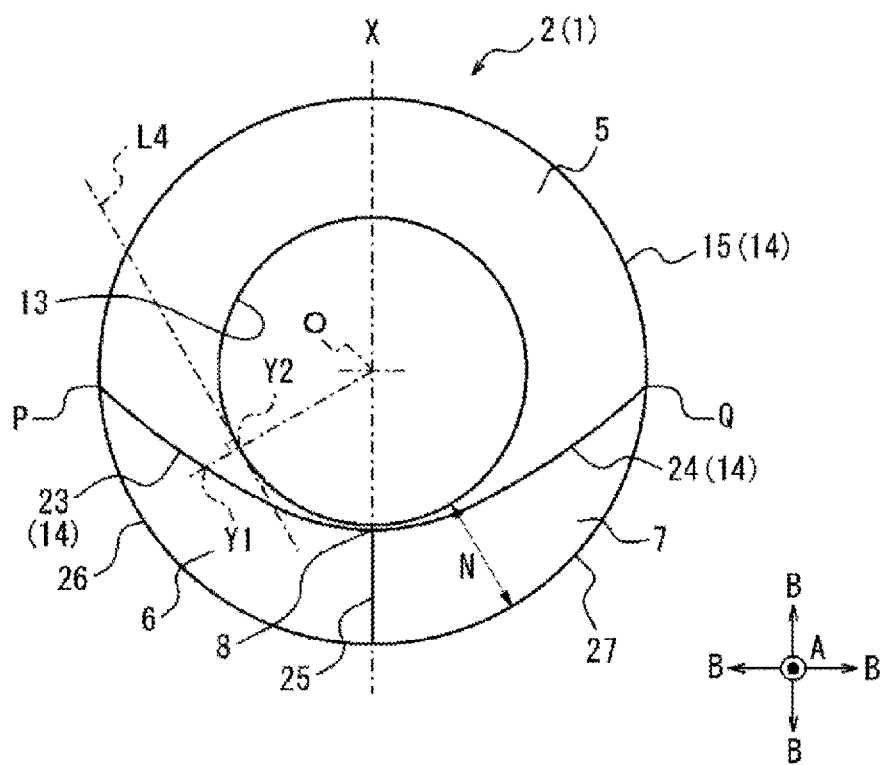
FIG. 3 is a view of the main body of the puncture needle shown in FIG. 1 as viewed from a distal side in a central axis direction.

FIG. 3 is a view of the main body 2 viewed from the distal side in the central axis direction A. In the distal-end view in FIG. 3, the needle tip 8 in the present embodiment is located inward from the outer peripheral surface of the main body 2 in a radial direction B. In the distal-end view (see FIG. 3), the needle tip 8 is preferably located inward from the outer peripheral surface of the main body 2 in the radial direction B by a distance equal to or more than ⅓ of the thickness N of the peripheral wall of the main body 2, more preferably by a distance equal to or more than ½ of the thickness N of the peripheral wall of the main body 2, and most preferably by a distance equal to or more than ⅔ of the thickness N of the peripheral wall of the main body 2. With such a configuration, the blade tip having smaller blade tip angle α and satisfying predetermined strength can be easily achieved.

In the distal-end view shown in FIG. 3, the first blade edge 23 curves in a concave shape from the needle tip 8 in the radial direction B. The second blade edge 24 curves in a concave shape from the needle tip 8 in the radial direction B. The first blade edge 23 curves along the entire length thereof and extends from the needle tip 8 to a proximal end P of the first blade edge. The second blade edge 24 curves along the entire length thereof and extends from the needle tip 8 to a proximal end Q of the second blade edge. The first blade edge 23 and the second blade edge 24 curve in a symmetrical manner with respect to the central plane X. The first blade edge 23 and the second blade edge 24 curve such that curvature radius become smaller with nearness to the needle tip 8. The curvature radius of the curvature of the first blade edge 23 or the second blade edge 24 at the proximal end P or the proximal end Q is the largest in the range from the needle tip 8 to the proximal end P or the proximal end Q. The curvature radius of the curvature of the first blade edge 23 or the second blade edge 24 at the needle tip 8 is the smallest in the range from the needle tip 8 to the proximal end P or the proximal end Q.

In the distal-end view shown in FIG. 3, the distance between the first blade edge 23 and the inner edge 13 of the first blade surface portion 5 gradually decreases from the proximal end P of the first blade edge 23 toward the needle tip 8. In the distal-end view shown in FIG. 3, the distance between the second blade edge 24 and the inner edge 13 of the first blade surface portion 5 gradually decreases from the proximal end Q of the second blade edge toward the needle tip 8. In the distal-end view shown in FIG. 3, the distance between each of the first blade edge 23 and the second blade edge 24 and the inner edge 13 of the first blade surface portion 5 is minimum at the needle tip 8. This distance means the shortest distance from an arbitrary point Y1 on each of the first blade edge 23 and the second blade edge 24 to the inner edge 13 of the first blade surface portion 5 in the distal-end view (see FIG. 3). A point Y2 on the inner edge 13 where the shortest distance is obtained is determined to be a position where a tangent line L4 of the inner edge 13 at this point Y2 is perpendicular to a straight line from the arbitrary point Y1 on each of the first blade edge 23 and the second blade edge 24 to the point Y2 on the inner edge 13.

In the distal-end view in FIG. 3, the first blade edge 23 does not intersect with or contact the inner edge 13 of the first blade surface portion 5 between the needle tip 8 and the proximal end P of the first blade edge 23. In the distal-end view in FIG. 3, the second blade edge 24 does not intersect with or contact the inner edge 13 of the first blade surface portion 5 between the needle tip 8 and the proximal end Q of the second blade edge 24.

In the distal-end view in FIG. 3, the fourth blade edge 26 extends, while curving, from the proximal end P of the first blade edge 23 to reach one end of the third blade edge 25. Similarly, in the distal-end view in FIG. 3, the fifth blade edge 27 extends, while curving, from the proximal end Q of the second blade edge 24 to reach one end of the third blade edge 25. In the distal-end view shown in FIG. 3, the first blade edge 23 curves more gently than the fourth blade edge 26. Similarly, in the distal-end view shown in FIG. 3, the second blade edge 24 curves more gently than the fifth blade edge 27.

The concave surface constituting the first blade surface portion 5 may include a concave curved surface or a flat surface. That is, the concave surface constituting the first blade surface portion 5 may be, for example, a concave surface formed by connecting a plurality of flat surfaces (see FIG. 10). Further, the concave surface constituting the first blade surface portion 5 may be a concave surface including both a concave curved surface and a flat surface. However, the concave surface constituting the first blade surface portion 5 preferably includes a concave curved surface. That is, it is more preferable that the concave surface is constituted by a concave curved surface as in the present embodiment. When the first blade surface portion 5 is constituted by a concave curved surface as in the present embodiment, a corner formed by a ridge line where the surfaces meet in the first blade surface portion 5 is not formed. Therefore, an increase in puncture resistance during puncture due to the corner can be prevented.

The front blade surface in the present embodiment is constituted only by the first blade surface portion 5, and the proximal end of the first blade surface portion 5 is contiguous to the outer peripheral surface of the main body 2. However, the configuration is not limited thereto, and a fourth blade surface portion that is contiguous to the proximal side of the first blade surface portion 5 may be formed. Similar to the first blade surface portion 5, the fourth blade surface portion extends linearly in the side view (see FIGS. 1(b) and 2(b)). The fourth blade surface portion may be constituted by one flat surface inclined with respect to the central axis direction A, or may be constituted by a plurality of continuous flat surfaces inclined with respect to the central axis direction A, in the side view (see FIGS. 1(b) and 2(b)). Further, the fourth blade surface portion may be a convex curved surface that is inclined with respect to the central axis direction A in the side view (see FIGS. 1(b) and 2(b)). Note that the fourth blade surface portion is preferably a convex curved surface that is smoothly contiguous to the proximal end of the first blade surface portion 5. With this configuration, the proximal end of the first blade surface portion 5 and the outer peripheral surface of the main body 2 can be smoothly connected by means of the fourth blade surface portion, whereby the puncture resistance during puncture at the position between the proximal end of the first blade surface portion 5 and the outer peripheral surface of the main body 2 can be reduced, compared to the configuration where the proximal end of the first blade surface portion 5 is contiguous to the outer peripheral surface of the main body 2.

However, even when the fourth blade surface portion is provided, the proximal side of a distal-end opening 11, which is one end of the hollow portion 10 on the distal side, is defined by the first blade surface portion 5. This configuration can prevent the skin from entering into the living body when the proximal end of the distal-end opening 11 passes through the skin during puncture.

The inner edge 13 of the first blade surface portion 5 in the present embodiment defines the distal-end opening 11, which is one end of the hollow portion 10 on the distal side. In the present embodiment, the inner edge 13 of the first blade surface portion 5 extends from the distal side to the proximal side of the main body 2 from the distal end to the proximal end in the central axis direction A. More specifically, in the present embodiment, out of two points where the inner edge 13 of the first blade surface portion 5 intersects with the central plane X, the point on the distal side of the main body 2 is the distal end of the inner edge 13 of the first blade surface portion 5 (see a point "F" in FIG. 2(a)), and the point on the proximal side of the main body 2 is the proximal end of the inner edge 13 of the first blade surface portion 5 (see a point "R" in FIG. 2(a)). The inner edge 13 of the first blade surface portion 5 constantly extends from the distal side to the proximal side of the main body 2 from the distal end (see the point "F" in FIG. 2(a)) to the proximal end (see the point "R" in FIG. 2(a)), and there is no portion extending from the proximal side to the distal side. The distal-end opening 11 has a teardrop shape when viewed from front (see FIG. 2(a)).

Further, the outer edge 14 of the first blade surface portion 5 in the present embodiment is constituted by the first blade edge 23 and the second blade edge 24, which have the needle tip 8 as one end, and a proximal-side outer edge portion 15. The details of the first blade edge 23 and the second blade edge 24 will be described later. The outer edge 14 of the first blade surface portion 5 defines a blade surface region T where the blade surface 4 is formed. Therefore, the maximum length of the outer edge of the blade surface 4 in the central axis direction A is the abovementioned blade surface length H (see FIG. 2(a)).

[Second Blade Surface Portion 6 and Third Blade Surface Portion 7]

The second blade surface portion 6 and the third blade surface portion 7 are each constituted by a flat surface. The second blade surface portion 6 and the third blade surface portion 7 are symmetrical with respect to the central plane X. The second blade surface portion 6 and the third blade surface portion 7 form, on the needle tip 8 side in the central axis direction A, the abovementioned third blade edge 25 having the needle tip 8 as one end by the ridge line where the second blade surface portion 6 and the third blade surface portion 7 meet. The third blade edge 25 in the present embodiment is straight, and the third blade edge 25 also extends on the central plane X.

Although the second blade surface portion 6 and the third blade surface portion 7 in the present embodiment are symmetrical with respect to the central plane X as described above, they may be asymmetrical with respect to the central plane X. However, if the second blade surface portion 6 and the third blade surface portion 7 are symmetrical with respect to the central plane X as in the present embodiment, the first blade edge 23 and the second blade edge 24 are also symmetrical with respect to the central plane X. Therefore, during puncture, variation in puncture resistance is less likely to occur at each side of the central plane X, and straightness of the puncture needle 1 can be further improved.

The angles of the second blade surface portion 6 and the third blade surface portion 7 with respect to the central plane X in a cross section perpendicular to the central axis direction A will be described later with reference to FIGS. 4(a) to 4(e).

Further, the second blade surface portion 6 in the present embodiment extends to the proximal side beyond a midpoint M of the blade surface region T in the central axis direction A. With this configuration, a wide area of the second blade surface portion 6 can be ensured, so that straightness during puncture can be improved. Further, the length of the later-described first blade edge 23 formed by the ridge line where the first blade surface portion 5 and the second blade surface portion 6 meet can be relatively increased.

Further, the third blade surface portion 7 in the present embodiment extends to the proximal side beyond the midpoint M of the blade surface region T in the central axis direction A. With this configuration, a wide area of the third blade surface portion 7 can be ensured, so that straightness during puncture can be improved. Further, the length of the later-described second blade edge 24 formed by the ridge line where the first blade surface portion 5 and the third blade surface portion 7 meet can be relatively increased. In addition, in the front view of the main body 2 (see FIGS. 1(a) and 2(a)), the tip angle β at the position of the needle tip 8 can be reduced.

As described above, due to the configuration in which both the first blade edge 23 and the second blade edge 24 are increased in length, the sum of the lengths of the first blade edge 23 and the second blade edge 24, that is, the length from the proximal end P (see FIG. 2(a)) of the first blade edge 23 to the proximal end Q (see FIG. 2(a)) of the second blade edge 24 via the needle tip 8 on the outer edge 14 of the first blade surface portion 5, can be increased. As a result, the width W (see FIG. 2(a)) of the cutting edge capable of cutting the skin by the first blade edge 23 and the second blade edge 24 during puncture using the puncture needle 1 can be increased. Increasing the width W of the cutting edge can prevent a cut part of the skin from being forcibly expanded after passage of the cutting edge. Therefore, the pain experienced by the patient during puncture can be decreased. Accordingly, from the viewpoint of puncture resistance, it is preferable to make the width W of the cutting edge close to the outer diameter of the main body 2.

However, the second blade surface portion 6 and the third blade surface portion 7 may terminate at the midpoint M of the blade surface region T in the central axis direction A or distal side from the midpoint M. Such a configuration can prevent the thickness of the needle at the position where the second blade surface portion 6 and the third blade surface portion 7 are not formed from being excessively reduced, thereby being capable of preventing a decrease in the strength of the needle. Furthermore, this configuration can also prevent the thickness from being excessively reduced, whereby defective products are less likely to be generated in the manufacturing process.

Further, the first blade edge 23 in the present embodiment has a concave shape in the front view of the main body 2 viewed from the first blade surface portion 5 side (see FIGS. 1(a) and 2(a)). More specifically, the first blade edge 23 in the present embodiment is constituted by a concave curved line in the front view of the main body 2 (see FIGS. 1(a) and 2(a)). When the first blade edge 23 is configured as described above, the tip angle β at the position of the needle tip 8 in the front view of the main body 2 can be reduced as shown in FIG. 2(a). Thus, the puncture resistance in the vicinity of the needle tip 8 during puncture can be further reduced.

In the present embodiment, the second blade edge 24 as well as the first blade edge 23 have a concave shape in the front view of the main body 2 (see FIGS. 1(a) and 2(a)). Therefore, as shown in FIG. 2(a), the tip angle β at the position of the needle tip 8 in the front view of the main body 2 can be further reduced, as compared with the configuration in which only the first blade edge 23 has a concave shape. Thus, the puncture resistance in the vicinity of the needle tip 8 during puncture can be reduced still further.

The first blade edge 23 and the second blade edge 24 in the present embodiment form a concave curved line in the front view of the main body 2 (see FIGS. 1(a) and 2(a)). However, they are not limited to have the above configuration. The concave shape may be formed by connecting a plurality of straight lines. However, using the first blade edge 23 and the second blade edge 24 that form a concave curved line in the front view (see FIGS. 1(a) and 2(a)) of the main body 2, as in the present embodiment, eliminates formation of a corner at a joint portion between straight lines. Therefore, an increase in puncture resistance during puncture due to the corner can be prevented.

Next, angles of the first blade surface portion 5, the second blade surface portion 6, and the third blade surface portion 7 with respect to the central plane X in a cross section perpendicular to the central axis direction A will be described. FIGS. 4(a), 4(b), 4(c), 4(d), and 4(e) are sectional views taken along lines I-I, II-II, III-III, IV-IV, and V-V in FIG. 2, respectively. The main body 2 in the present embodiment has a symmetrical structure with respect to the central plane X.

Figure 4A:
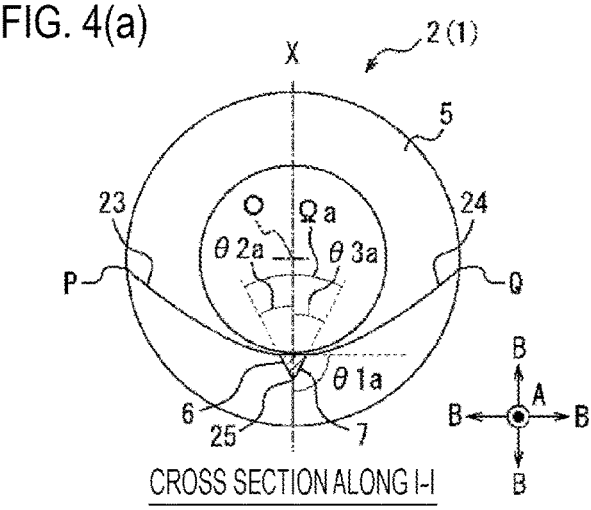
FIGS. 4(a), 4(b), 4(c), 4(d), and 4(e) are sectional views taken along lines I-I, II-II, III-III, IV-IV, and V-V in FIG. 2, respectively.

FIG. 4(a) shows a cross section along the line I-I in FIG. 2, that is, a cross section perpendicular to the central axis direction A at a position where the third blade edge 25 is formed in the central axis direction A. As shown in FIG. 4(a), an angle θ1a of the first blade surface portion 5 with respect to the central plane X in the cross section along the line I-I in FIG. 2 is 90 degrees. In other words, in the cross section along the line I-I in FIG. 2, the first blade surface portion 5 extends linearly in a direction perpendicular to the central plane X.

As shown in FIG. 4(a), the second blade surface portion 6 extends so as to incline at an acute angle θ2a with respect to the central plane X in the cross section along the line I-I in FIG. 2. Further, in FIG. 4(a), the third blade surface portion 7 also extends so as to incline at an acute angle θ3a with respect to the central plane X. As described above, the second blade surface portion 6 and the third blade surface portion 7 are symmetrical with respect to the central plane X. Therefore, in FIG. 4(a), the angle θ2a of the second blade surface portion 6 is equal to the angle θ3a of the third blade surface portion 7.

In FIG. 4(a), a sectional angle Ωa between the second blade surface portion 6 and the third blade surface portion 7 is equal to the sum of the angle θ2a of the second blade surface portion 6 with respect to the central plane X and the angle θ3a of the third blade surface portion 7 with respect to the central plane X.

Figure 4B:
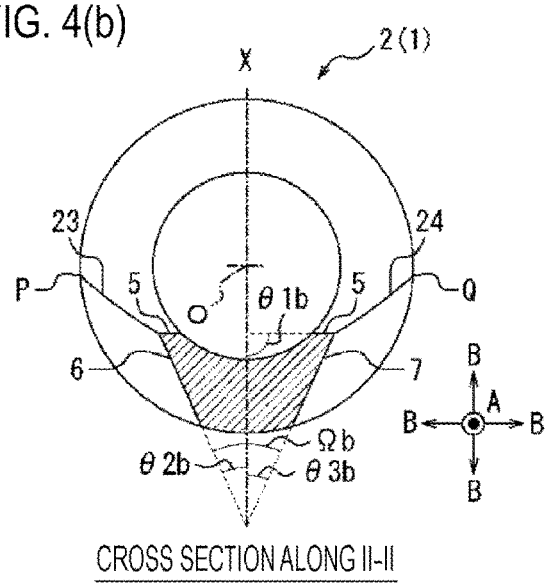

FIG. 4(b) shows a cross section along the line II-II in FIG. 2, that is, a cross section perpendicular to the central axis direction A at the position where the third blade edge 25 is not formed in the central axis direction A, and the second blade surface portion 6 and the third blade surface portion 7 are formed in the central axis direction A. As shown in FIG. 4(b), an angle θ1b of the first blade surface portion 5 with respect to the central plane X in the cross section along the line II-II in FIG. 2 is 90 degrees. In other words, in the cross section along the line II-II in FIG. 2, the first blade surface portion 5 extends linearly in a direction perpendicular to the central plane X.

As shown in FIG. 4(b), the second blade surface portion 6 extends so as to incline at an acute angle θ2b with respect to the central plane X, in the cross section along the line II-II in FIG. 2. This angle θ2b is equal to the angle θ2a in FIG. 4(a). Further, in FIG. 4(b), the third blade surface portion 7 also extends so as to incline at an acute angle θ3b with respect to the central plane X. This angle θ3b is equal to the angle θ3a in FIG. 4(a). Therefore, in FIG. 4(b), the angle θ2b of the second blade surface portion 6 and the angle θ3b of the third blade surface portion 7 are equal to each other.

In FIG. 4(b), a sectional angle Ωb between the second blade surface portion 6 and the third blade surface portion 7 is equal to the sum of the angle θ2b of the second blade surface portion 6 with respect to the central plane X and the angle θ3b of the third blade surface portion 7 with respect to the central plane X. Therefore, the sectional angle Ωa in FIG. 4(a) and the sectional angle Ωb in FIG. 4(b) are equal to each other.

Figure 4C:
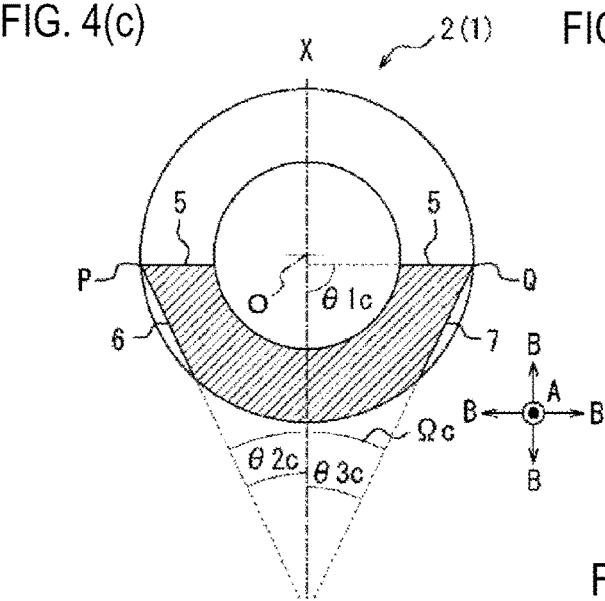

FIG. 4(c) shows a cross section along the line III-III in FIG. 2, that is, a cross section perpendicular to the central axis direction A at the position that is further on the proximal side of the main body 2 as compared to the cross section along the line II-II in FIG. 2, and at which the third blade edge 25 is not formed in the central axis direction A, and the second blade surface portion 6 and the third blade surface portion 7 are formed in the central axis direction A. As shown in FIG. 4(c), an angle θ1c of the first blade surface portion 5 with respect to the central plane X in the cross section along the line III-III in FIG. 2 is 90 degrees. In other words, in the cross section along the line III-III in FIG. 2, the first blade surface portion 5 extends linearly in a direction perpendicular to the central plane X.

As shown in FIG. 4(c), the second blade surface portion 6 extends so as to incline at an acute angle θ2c with respect to the central plane X, in the cross section along the line III-III in FIG. 2. This angle θ2c is equal to the angles θ2a and θ2b in FIGS. 4(a) and 4(b). Further, in FIG. 4(c), the third blade surface portion 7 also extends so as to incline at an acute angle θ3c with respect to the central plane X. This angle θ3c is equal to the angles θ3a and θ3b in FIGS. 4(a) and 4(b). Therefore, in FIG. 4(c), the angle θ2c of the second blade surface portion 6 and the angle θ3c of the third blade surface portion 7 are equal to each other.

In FIG. 4(c), a sectional angle Ωc between the second blade surface portion 6 and the third blade surface portion 7 is equal to the sum of the angle θ2c of the second blade surface portion 6 with respect to the central plane X and the angle θ3c of the third blade surface portion 7 with respect to the central plane X. Therefore, the sectional angles Ωa and Ωb in FIGS. 4(a) and 4(b) are equal to the sectional angle Ωc in FIG. 4(c).

Figure 4D:
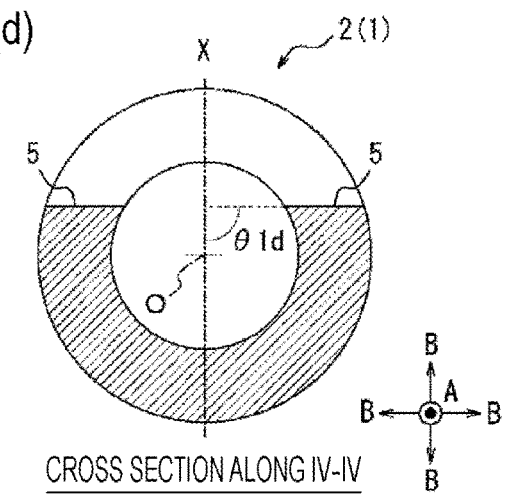

FIG. 4(d) shows a cross section along the line IV-IV in FIG. 2, that is, a cross section perpendicular to the central axis direction A at the position where the second blade surface portion 6 and the third blade surface portion 7 are not formed in the central axis direction A, and the first blade surface portion 5 is formed. As shown in FIG. 4(d), an angle θ1d of the first blade surface portion 5 with respect to the central plane X in the cross section along the line IV-IV in FIG. 2 is 90 degrees. In other words, in the cross section along the line IV-IV in FIG. 2, the first blade surface portion 5 extends linearly in a direction perpendicular to the central plane X.

Figure 4E:
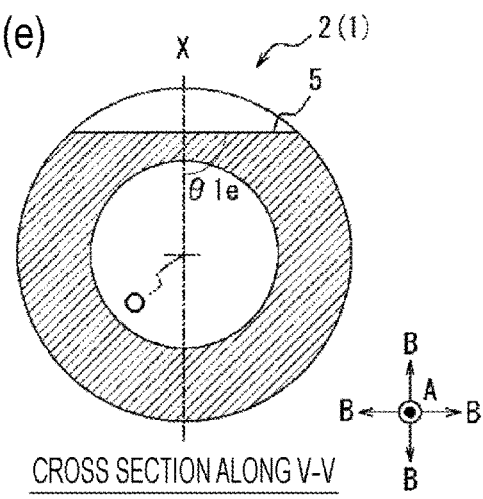

FIG. 4(e) shows a cross section along the line V-V in FIG. 2, that is, a cross section perpendicular to the central axis direction A at the position that is further on the proximal side of the main body 2 as compared to the cross section along the line IV-IV in FIG. 2, and at which the first blade surface portion 5 is formed. As shown in FIG. 4(e), an angle θ1e of the first blade surface portion 5 with respect to the central plane X in the cross section along the line V-V in FIG. 2 is 90 degrees. In other words, in the cross section along the line V-V in FIG. 2, the first blade surface portion 5 extends linearly in a direction perpendicular to the central plane X.

As described above, the first blade surface portion 5 extends perpendicular to the central plane X in an arbitrary cross section that includes the first blade surface portion 5 and that is perpendicular to the central axis direction A (see the angles θ1a to θ1e in FIGS. 4(a) to 4(e)). In other words, the angle θ1 of the first blade surface portion 5 in the cross section perpendicular to the central axis direction A is constant regardless of the position in the central axis direction A.

The second blade surface portion 6 is inclined at an equal angle with respect to the central plane X in an arbitrary cross section that includes the second blade surface portion 6 and that is perpendicular to the central axis direction A (see the angles θ2a to θ2c in FIGS. 4(a) to 4(c)). In other words, the angle θ2 of the second blade surface portion 6 in a cross section perpendicular to the central axis direction A is constant regardless of the position in the central axis direction A.

The third blade surface portion 7 is inclined at an equal angle with respect to the central plane X in an arbitrary cross section that includes the third blade surface portion 7 and that is perpendicular to the central axis direction A (see the angles θ3a to θ3c in FIGS. 4(a) to 4(c)). In other words, the angle θ3 of the third blade surface portion 7 in a cross section perpendicular to the central axis direction A is constant regardless of the position in the central axis direction A.

Therefore, the sectional angle Ω is also constant regardless of the position in the central axis direction A (see the sectional angles Ωa to Ωc in FIGS. 4(a) to 4(c)).

In addition, the angle θ2 of the second blade surface portion 6 in a cross section perpendicular to the central axis direction A is equal to the angle θ3 of the third blade surface portion 7 in a cross section perpendicular to the central axis direction A, regardless of the position in the central axis direction A.

Second Embodiment

Figure 6A:
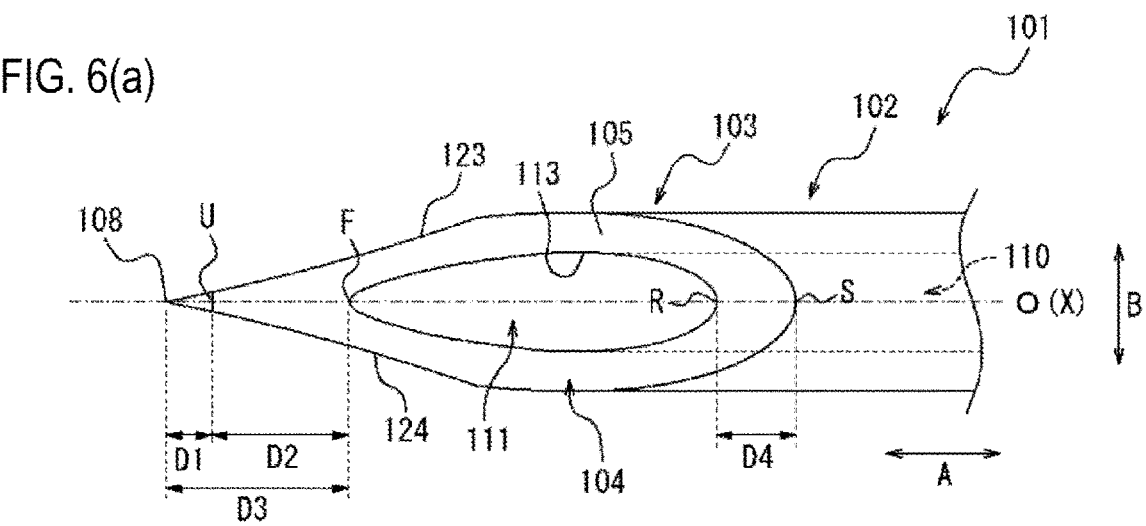
FIGS. 6(a), 6(b), and 6(c) are a front view, a side view, and a rear view of a puncture needle as one embodiment, respectively.
Figure 6B:
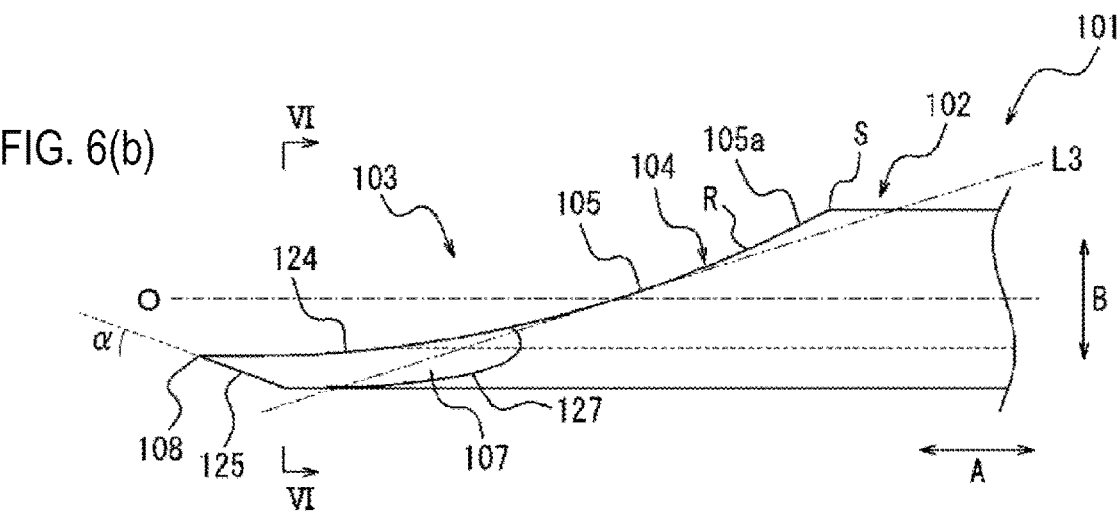
Figure 6C:
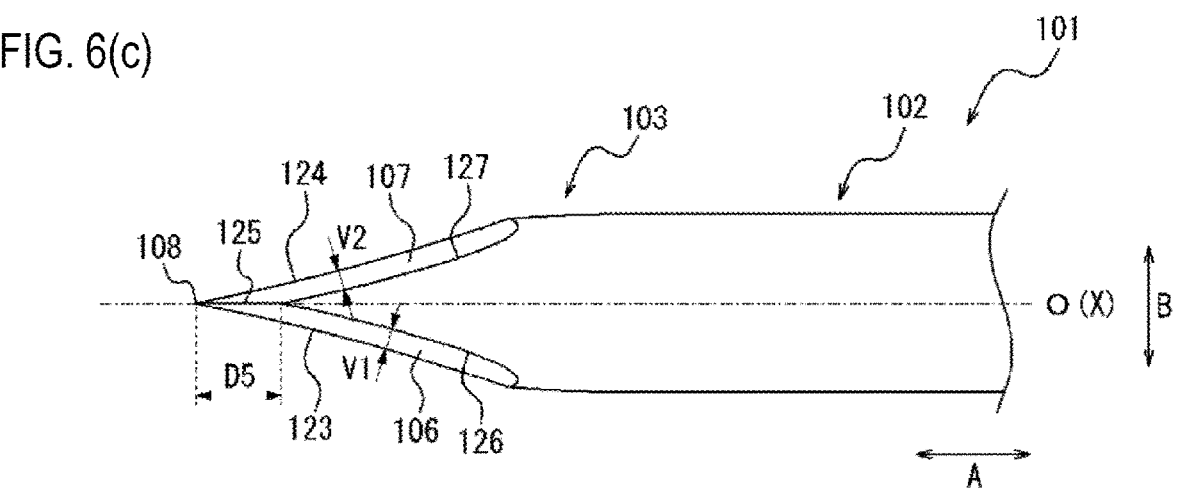
Figure 7:
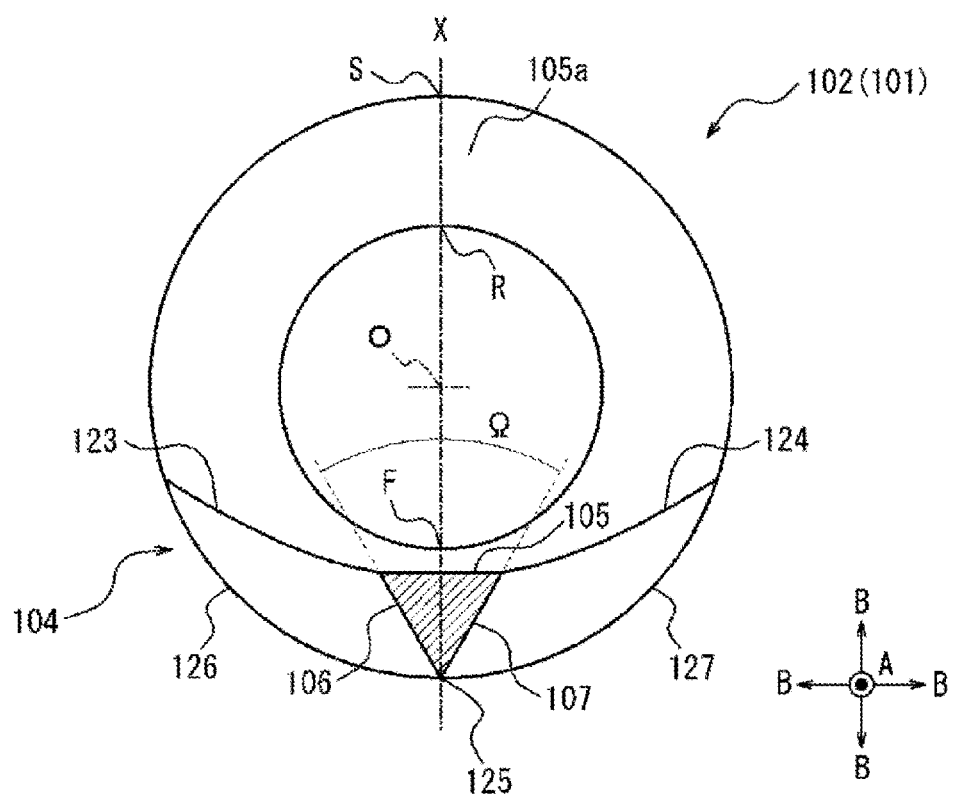
FIG. 7 is a sectional view taken along a line VI-VI in FIG. 6(b).

Next, a puncture needle according to another embodiment will be described. FIGS. 6(a), 6(b), 6(c), and 7 are views showing a puncture needle 101 as a second embodiment. Specifically, FIGS. 6(a), 6(b), and 6(c) are a front view, a side view, and a rear view of the puncture needle 101, respectively. FIG. 7 is a sectional view taken along a line VI-VI in FIG. 6(b), showing a cross section perpendicular to the central axis O at the position of a proximal end of a third blade edge 125 of the puncture needle 101. A blade surface 104 of the puncture needle 101 includes a first blade surface portion 105, a second blade surface portion 106, and a third blade surface portion 107.

As shown in FIGS. 6 and 7, the puncture needle 101 includes a main body 102 having a hollow portion 110, and the blade surface 104 is formed at a distal end portion 103 of the main body 102. The first blade surface portion 105 has a symmetrical shape with respect to a central plane X, which is a virtual plane, passing through a needle tip 108 and including a central axis O. An inner edge 113 of the first blade surface portion 105 defines a distal-end opening 111 of the hollow portion 110.

The first blade surface portion 105 linearly extends substantially perpendicular to the central plane X at an arbitrary cross section perpendicular to the central axis direction A at the position of the first blade surface portion 105. In other words, the first blade surface portion 105 appears linear when viewed from a direction perpendicular to the central plane X, that is, in a side view (see FIG. 6(b)).

The first blade surface portion 105 is constituted by a concave surface that is concave in the side view (see FIG. 6(b)). The "concave surface" is not limited to a single curved surface having a concave shape, and is not particularly limited, as long as it is a concave surface in the side view (see FIG. 6(b)) of the main body 102 in which the first blade surface portion 105 appears linear. For example, the concave surface may be constituted by a plurality of continuous flat surfaces. As shown in FIGS. 6(a) and (b), the concave surface of the first blade surface portion 105 includes a gentle curved surface that extends from a proximal end S of a jaw part of the first blade surface portion 105 as a starting end to a terminal end U located proximal to the needle tip 108. The concave curved surface of the first blade surface portion 105 has a curvature having a radius around a point (not shown) located above the first blade surface portion 105 in FIG. 6(b). The inner edge 113 of the first blade surface portion 105 extends substantially elliptically from the proximal end R in substantially a symmetrical manner with respect to the central plane X and reaches a distal end F of the inner edge 113. The portion distal to the terminal end U of the concave curved surface of the first blade surface portion 105 extends to the needle tip 108 as a flat surface parallel to the central axis O.

As shown in FIG. 6(a), in a front view as seen from the first blade surface portion 105 side, a length D1 from the needle tip 108 to the terminal end U of the concave curved surface of the first blade surface portion 105 is shorter than a length D2 from the terminal end U to the distal end F of the inner edge 113. A length D3 from the needle tip 108 to the distal end F of the inner edge 113 is longer than a length D4 from the proximal end R of the inner edge 113 of the first blade surface portion 105 to the proximal end S of the jaw part of the first blade surface portion 105.

As shown in FIG. 6(b), in the side view, a tangent line L3 of the first blade surface portion 105 at a point where the first blade surface portion 105 and the central axis O of the main body 102 intersect with each other intersects with the second blade surface portion 106 and the third blade surface portion 107. In FIG. 6(b), which is a view seen from the third blade surface portion 107 side, the tangent line L3 of the first blade surface portion 105 at the point where the first blade surface portion 105 intersects with the central axis O of the main body 102 intersects with the third blade surface portion 107. In a view seen from the second blade surface portion 106 side, the tangent line L3 intersects with the second blade surface portion 106. In the side view, a surface reverse to the first blade surface portion 105 is constituted by an outer peripheral surface of the main body 102, is linear in parallel with the central axis O, and extends to a proximal end of the third blade edge 125.

In the side view in FIG. 6(b), the concave surface constituting the first blade surface portion 105 overlaps the second blade surface portion 106 and the third blade surface portion 107 in the central axis direction A. The proximal ends of the second blade surface portion 106 and the third blade surface portion 107 are located between the distal end and the proximal end of the concave surface of the first blade surface portion 105. Specifically, the concave surface of the first blade surface portion 105 extends from the proximal end S of the jaw part toward the needle tip 108. The proximal ends of the second blade surface portion 106 and the third blade surface portion 107 are located more proximally than the terminal end U of the curved surface of the first blade surface portion 105. The proximal ends of the second blade surface portion 106 and the third blade surface portion 107 are located more distally than the proximal end S of the jaw part. FIG. 6(b) shows the overlap between the first blade surface portion 105 and the third blade surface portion 107 in the central axis direction A. In the side view seen from the second blade surface portion 106 side reverse to that in FIG. 6(b), the overlap relationship between the first blade surface portion 105 and the second blade surface portion 106 in the central axis direction A is similar to that between the first blade surface portion 105 and the third blade surface portion 107 shown in FIG. 6(b).

As shown in FIG. 6(c), the second blade surface portion 106 and the third blade surface portion 107 are formed on the distal side of the blade surface 104. The second blade surface portion 106 and the third blade surface portion 107 are formed on the back side of the first blade surface portion 105. The second blade surface portion 106 forms a first blade edge 123 having the needle tip 108 as one end by a ridge line where the second blade surface portion 106 meets the first blade surface portion 105. The third blade surface portion 107 forms a second blade edge 124 having the needle tip 108 as one end by a ridge line where the third blade surface portion 107 meets the first blade surface portion 105. The second blade surface portion 106 and the third blade surface portion 107 form a third blade edge 125 having the needle tip 108 as one end by a ridge line where they meet. The second blade surface portion 106 and the outer peripheral surface of the main body 102 form a fourth blade edge 126 by a ridge line where they meet. The third blade surface portion 107 and the outer peripheral surface of the main body 102 form a fifth blade edge 127 by a ridge line where they meet.

In the rear view shown in FIG. 6(c), the first blade edge 123 is formed outside the second blade surface portion 106 in the radial direction B. In the rear view shown in FIG. 6(c), the fourth blade edge 126 is formed inside the second blade surface portion 106 in the radial direction B. In the rear view shown in FIG. 6(c), a region having a constant width V1 is formed between the first blade edge 123 and the fourth blade edge 126 in a direction along the first blade edge 123.

In the rear view shown in FIG. 6(c), the second blade edge 124 is formed outside the third blade surface portion 107 in the radial direction B. In the rear view shown in FIG. 6(c), the fifth blade edge 127 is formed inside the third blade surface portion 107 in the radial direction B. In the rear view shown in FIG. 6(c), a region having a constant width V2 is formed between the second blade edge 124 and the fifth blade edge 127 in a direction along the second blade edge 124.

As shown in FIG. 6(c), the length D5 of the third blade edge 125 in the central axis direction A in the rear view is shorter than the length D3 described above. The length D5 in the rear view is longer than the length D1 described above.

Next, the overview and results of a puncture resistance test for five puncture needles having different blade tip angles α and different sectional angles Ω will be described. Hereinafter, for convenience of description, the prepared five puncture needles will be referred to as first to fifth test pieces. Each of the first to fifth test pieces is a puncture needle according to an embodiment of the present invention. The puncture needle prepared as the first test piece has a blade tip angle α of 15 degrees and a sectional angle Ω of 85 degrees. The puncture needle prepared as the second test piece has a blade tip angle α of 20 degrees and a sectional angle Ω of 60 degrees. The puncture needle prepared as the third test piece has a blade tip angle α of 20 degrees and a sectional angle Ω of 85 degrees. The puncture needle prepared as the fourth test piece has a blade tip angle α of 30 degrees and a sectional angle Ω of 60 degrees. The puncture needle prepared as the fifth test piece has a blade tip angle α of 40 degrees and a sectional angle Ω of 60 degrees.

Here, the puncture needle 101 shown in FIGS. 6 and 7 is used as the second test piece. As described above, the blade surface 104 of the puncture needle 101 includes the first blade surface portion 105, the second blade surface portion 106, and the third blade surface portion 107. The overview of the puncture resistance test for the first to fifth test pieces will be described below. While the overview of the puncture resistance test will be described here as one example using the second test piece shown in FIGS. 6 and 7, which is one of the first to fifth test pieces, the overview of the puncture resistance test for the first and third to fifth test pieces is the same as the overview for the second test piece.

In the puncture resistance test, sheet-shaped urethane having a thickness of 0.3 mm is punctured using the puncture needle 101, and the puncture resistance is measured. In this test, DUS 605 (part number) of "Higress" (product name) (registered trademark) manufactured by Sheedom Co., Ltd. is used as the sheet-shaped urethane. The puncture angle of the puncture needle 101 into the urethane is 90 degrees. The puncture speed of the puncture needle 101 to the urethane is 50 nm/min. In this test, the measured parameters are the puncture resistance value [gf] when the needle tip 108 of the puncture needle 101 passes through the urethane, and the puncture resistance value [gf] when the proximal end S of a jaw part 105a (heel of the jaw part 105a) of the first blade surface portion 105 of the puncture needle 101 passes through the urethane. The puncture resistance of the blade surface 104 is the maximum at the proximal end S of the jaw part 105a of the first blade surface portion 105 of the puncture needle 101. The puncture resistance is measured using a micro load tester. In this test, the puncture resistance is measured using EZ-SX manufactured by Shimadzu Corporation. The puncture resistance at the position of the needle tip of the puncture needle is evaluated such that the puncture resistance value of 50 gf or less is preferable, the puncture resistance value of 40 gf or less is more preferable, and the puncture resistance value of 30 gf or less is most preferable. The puncture resistance at the position of the proximal end of the jaw part of the first blade surface portion of the puncture needle is evaluated such that the puncture resistance value of 60 gf or less is preferable, the puncture resistance value of 55 gf or less is more preferable, and the puncture resistance value of 50 gf or less is most preferable.

Further, the abovementioned puncture resistance test is repeated five times using the same puncture needle 101. When the puncture needle 101 is inserted into a blood vessel from the surface of a living body, the puncture needle 101 needs to puncturing not only the skin but also the fat layer, muscle, blood vessel wall, and the like. In other words, even in a single puncture, the puncture needle 101 may deform during puncturing through a plurality of sites having different properties in the middle of puncture before the needle tip 108 reaches the inside of the blood vessel. Here, the abovementioned puncture resistance test was repeated five times using the same puncture needle 101, and the durability of the puncture needle 101, more specifically, a possibility of an occurrence of deformation on the puncture needle 101 before the needle tip 108 reached the inside of the blood vessel, was evaluated. Here, when a rate of change of the puncture resistance at the position of the needle tip by five puncturing operations is 25% or less, and a rate of change of the puncture resistance at the position of the proximal end of the jaw part of the first blade surface portion by five puncturing operations is 15% or less, the puncture needle is evaluated to have durability by which the puncture needle is less likely to deform. In particular, when a rate of change of the puncture resistance at the position of the needle tip by five puncturing operations is 20% or less, and a rate of change of the puncture resistance at the position of the proximal end of the jaw part of the first blade surface portion by five puncturing operations is 10% or less, the puncture needle is evaluated to have durability by which no deformation of the puncture needle occurs. The rate of change of the puncture resistance by five puncturing operations means the ratio of the difference between the maximum value and the minimum value of the puncture resistance values by the five puncturing operations to the minimum value of the puncture resistance values by the five puncturing operations.

Table 1 below shows the results of the puncture resistance test for the first to fifth test pieces.

found that, according to the first to third test pieces, the puncture resistance at the position of the needle tip can be reduced still further.

Figure 9:
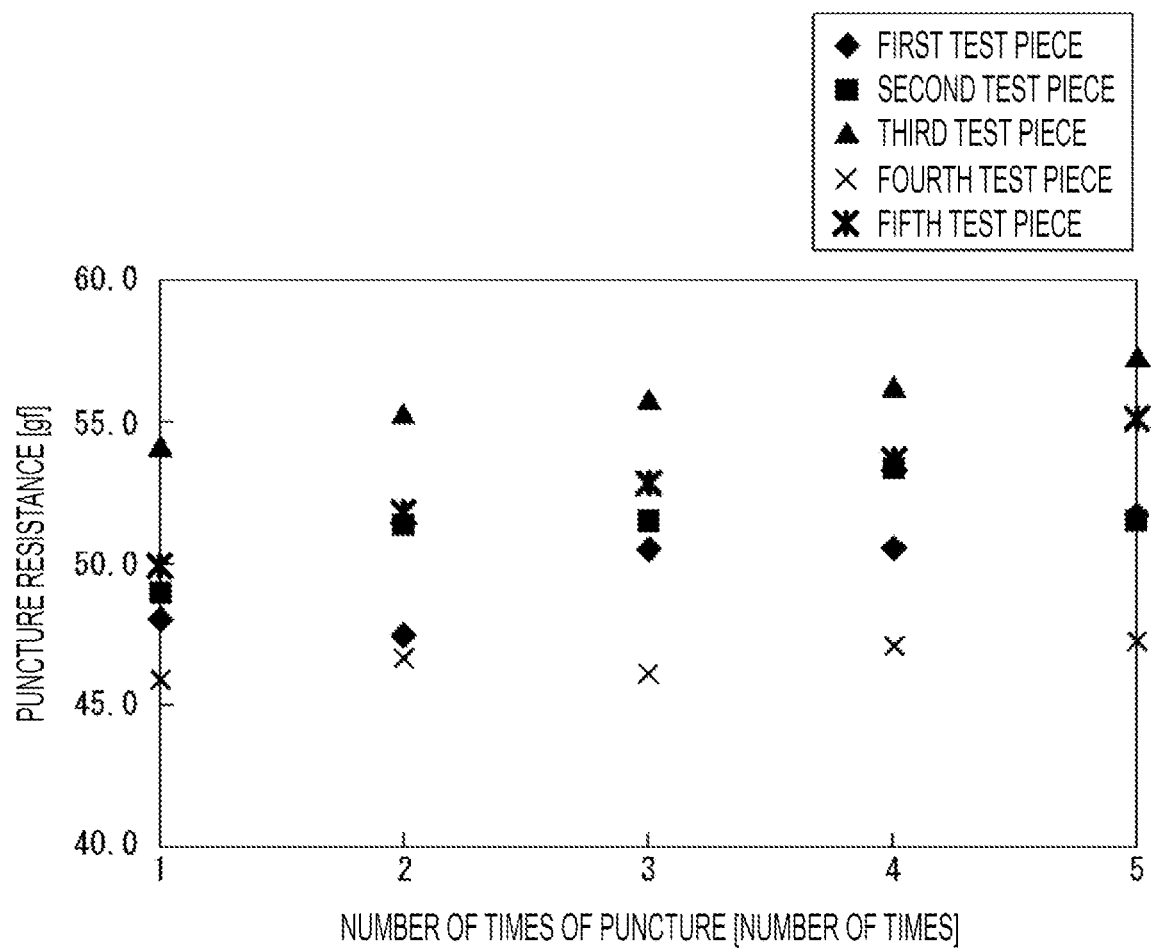
FIG. 9 is a graph showing a change in puncture resistance value at a proximal end of a jaw part of a first blade surface portion from a first puncture to a fifth puncture for each of first to fifth test pieces.

It can be seen from Table 1 and FIG. 9 that the puncture resistance values of the first to fifth test pieces at the position of the proximal end of the jaw part of the first blade surface portion in the first puncture are suppressed to 60 gf or less. Further, it can be seen from Table 1 and FIG. 9 that the puncture resistance values of the first to fifth test pieces at the position of the proximal end of the jaw part of the first blade surface portion in the first puncture are suppressed to 55 gf or less. Furthermore, it can be seen from Table 1 and FIG. 9 that the puncture resistance values of the first, second, fourth, and fifth test pieces at the position of the proximal end of the jaw part of the first blade surface portion in the first puncture are suppressed to 50 gf or less. Thus, it is found that, according to the first to fifth test pieces, the puncture resistance at the position of the proximal end of the jaw part of the first blade surface portion can be greatly reduced. It is also found that, according to the first, second, fourth, and fifth test pieces, the puncture resistance at the

TABLE 1

| | Blade tip angle α | Sectional angle Ω | Puncture resistance (first puncture) | | Puncture resistance (second puncture) | | Puncture resistance (third puncture) | | Puncture resistance (fourth puncture) | | Puncture resistance (fifth puncture) | |
|---|---|---|---|---|---|---|---|---|---|---|---|---|
| | | | Needle tip | Proximal end of jaw part | Needle tip | Proximal end of jaw part | Needle tip | Proximal end of jaw part | Needle tip | Proximal end of jaw part | Needle tip | Proximal end of jaw part |
| First test piece | 15° | 85° | 22.2 | 48.1 | 22.3 | 47.5 | 25.2 | 50.5 | 26.3 | 50.5 | 27.3 | 51.7 |
| Second test piece | 20° | 60° | 19.2 | 49.0 | 19.7 | 51.4 | 20.7 | 51.5 | 22.5 | 53.4 | 21.0 | 51.5 |
| Third test piece | 20° | 85° | 28.0 | 54.2 | 30.2 | 55.3 | 31.5 | 55.8 | 32.4 | 56.3 | 33.6 | 57.3 |
| Fourth test piece | 30° | 60° | 36.7 | 45.9 | 38.5 | 46.7 | 38.5 | 46.1 | 40.3 | 47.1 | 40.9 | 47.2 |
| Fifth test piece | 40° | 60° | 47.5 | 50.0 | 50.2 | 51.8 | 51.6 | 52.8 | 52.6 | 53.6 | 54.0 | 55.1 |

Figure 8:
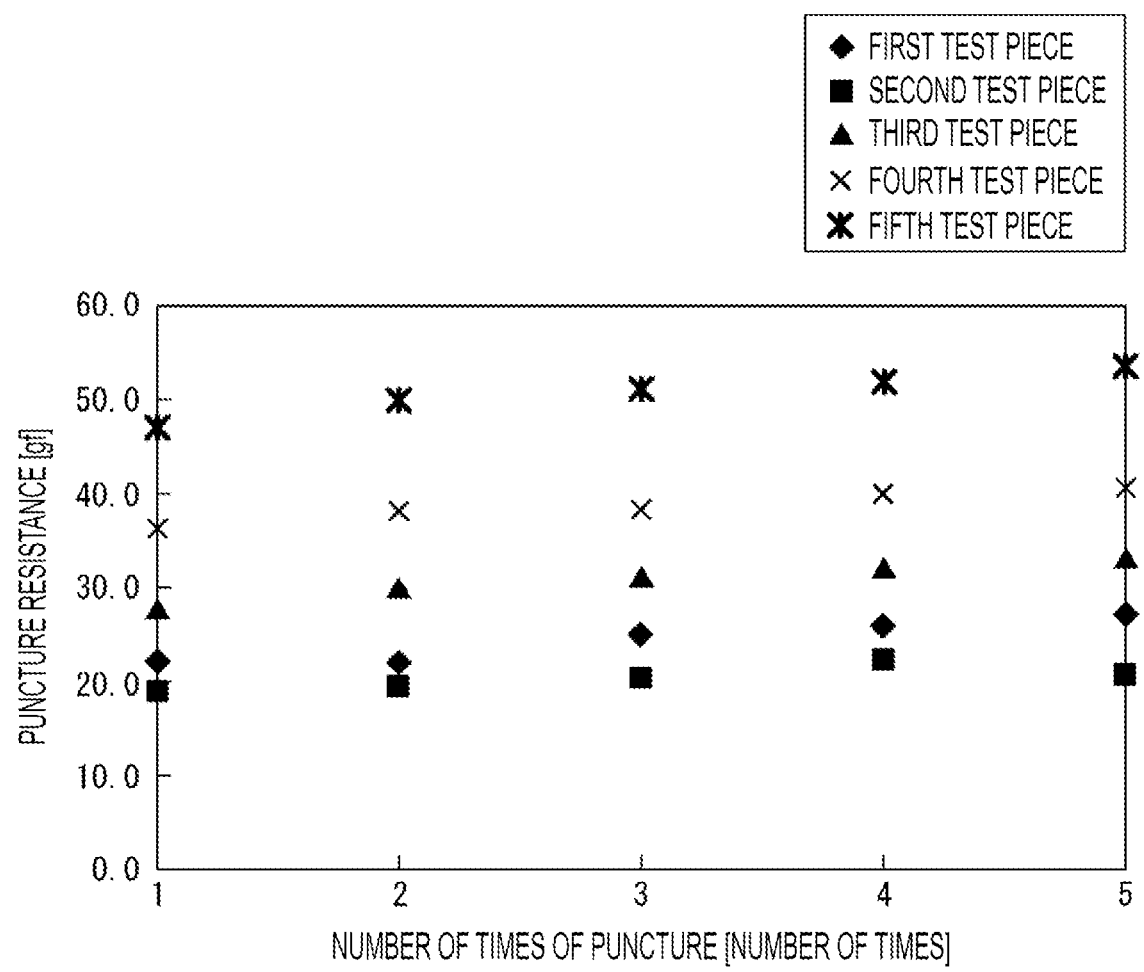
FIG. 8 is a graph showing a change in puncture resistance value at a needle tip from a first puncture to a fifth puncture for each of first to fifth test pieces.

FIG. 8 is a graph showing a change in puncture resistance value at the needle tip from the first puncture to the fifth puncture for each of the first to fifth test pieces. FIG. 9 is a graph showing a change in puncture resistance value at the proximal end of the jaw part of the first blade surface portion from the first puncture to the fifth puncture for each of the first to fifth test pieces.

It can be seen from Table 1 that the puncture resistance value at the needle tip and the puncture resistance value at the proximal end of the jaw part differ among the first to fifth test pieces having different combinations of the blade tip angle α and the sectional angle Ω. It can be seen from Table 1 and FIG. 8 that the puncture resistance values of the first to fifth test pieces at the position of the needle tip in the first puncture are suppressed to 50 gf or less. Further, it can be seen from Table 1 and FIG. 8 that the puncture resistance values of the first to fourth test pieces at the position of the needle tip in the first puncture are suppressed to 40 gf or less. Furthermore, it can be seen from Table 1 and FIG. 8 that the puncture resistance values of the first to third test pieces at the position of the needle tip in the first puncture are suppressed to 30 gf or less. Thus, it is found that, according to the first to fifth test pieces, the puncture resistance at the position of the needle tip can be reduced, and according to the first to fourth test pieces, the puncture resistance at the position of the needle tip can be further reduced. It is also position of the proximal end of the jaw part of the first blade surface portion can be reduced still further.

From the above, the blade tip angle α is preferably set within the range of 12 to 42 degrees, more preferably set within the range of 15 to 40 degrees, and still more preferably set within the range of 15 to 30 degrees. Further, the sectional angle Ω is preferably set within the range of 50 to 110 degrees, and more preferably set within the range of 60 to 85 degrees.

Table 2 below shows a rate of change of the puncture resistance of each of the first to fifth test pieces at the position of the needle tip by five puncturing operations, and a rate of change of the puncture resistance of the first to fifth test pieces at the position of the proximal end of the jaw part of the first blade surface portion by five puncturing operations.

TABLE 2

| | Rate of change (%) | |
|---|---|---|
| | Needle tip | Proximal end of jaw part |
| First test piece | 22.9 | 8.9 |
| Second test piece | 17.3 | 9.0 |

TABLE 2-continued

| | Rate of change (%) | |
|---|---|---|
| | Needle tip | Proximal end of jaw part |
| Third test piece | 19.8 | 5.8 |
| Fourth test piece | 11.5 | 2.9 |
| Fifth test piece | 13.6 | 10.2 |

As shown in Table 2, the rate of change of the puncture resistance of each of the first to fifth test pieces at the position of the needle tip by the five puncturing operations is smaller than 25%. In addition, the rate of change of the puncture resistance of each of the first to fifth test pieces at the position of the proximal end of the jaw part of the first blade surface portion by the five puncturing operations is smaller than 15%. Therefore, the first to fifth test pieces can be evaluated to have durability by which deformation is less likely to occur during puncture.

Further, as shown in Table 2, the rate of change of the puncture resistance of each of the second to fifth test pieces at the position of the needle tip by the five puncturing operations is smaller than 20%. In addition, the rate of change of the puncture resistance of each of the first to fourth test pieces at the position of the proximal end of the jaw part of the first blade surface portion by the five puncturing operations is smaller than 10%. Therefore, the second to fourth test pieces can be evaluated to have durability by which deformation does not occur during puncture.

It is found from the above that the puncture needle having a combination of the blade tip angle α of 20 degrees and the sectional angle Ω of 60 degrees, that is, the puncture needle 101 as the second test piece shown in FIGS. 6 and 7, is the most preferable example among the first to fifth test pieces from the viewpoint of puncture resistance and durability.

Lastly, a method for manufacturing the puncture needle 1 described above will be described. The blade surface 4 of the main body 2 of the puncture needle 1 is formed by grinding a distal end portion of a tubular member by cutting, grinding, electro-discharge (including wire electric discharge) machining, or the like. Specifically, the distal end portion of the tubular member is ground by cutting, grinding, electro-discharge (including wire electric discharge) machining, or the like to form the first blade surface portion 5, the second blade surface portion 6, and the third blade surface portion 7. In this way, the blade surface 4 of the main body 2 can be formed.

Figure 10:
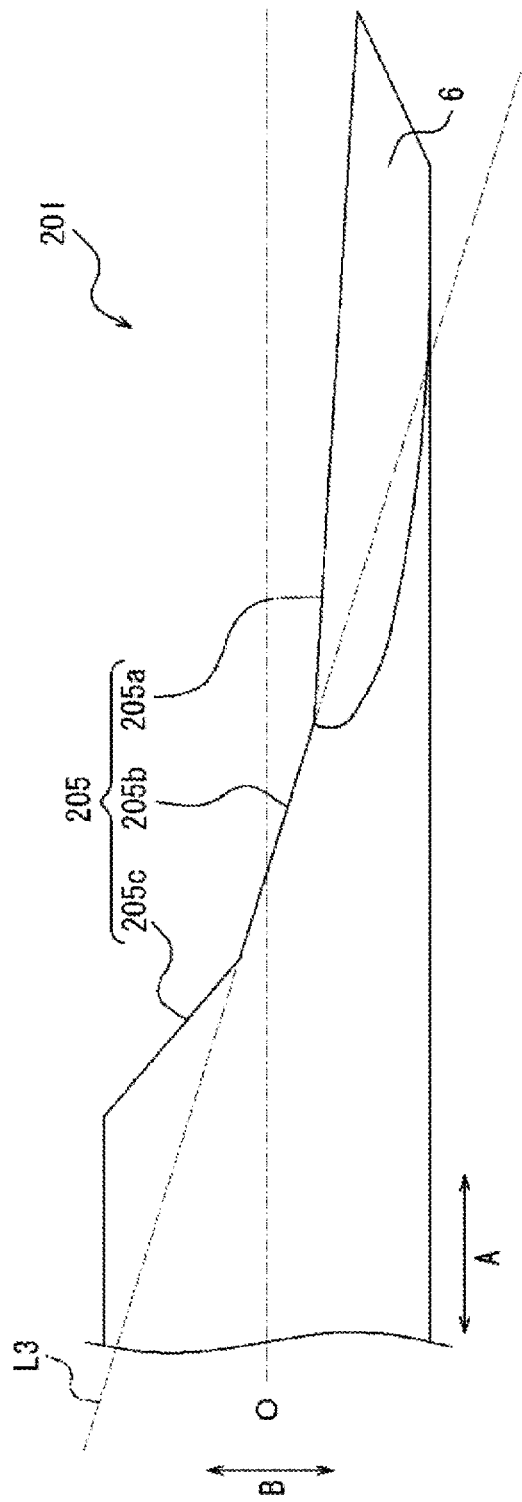
FIG. 10 is a side view showing a first blade surface portion as a modification of the first blade surface portion shown in FIG. 1.

The puncture needle according to the present disclosure is not limited to have the specific configuration indicated in the above embodiments, and various modifications and changes are possible without departing from the scope of the claims. As described above, the concave surface constituting the first blade surface portion 5 may have a concave curved surface or a flat surface as shown in FIG. 10. FIG. 10 shows a puncture needle 201 including a first blade surface portion 205 constituted by a concave surface formed by connecting a plurality of flat surfaces. Specifically, the first blade surface portion 205 shown in FIG. 10 includes a first flat surface 205a, a second flat surface 205b, and a third flat surface 205c. The first flat surface 205a is inclined at a predetermined angle with respect to the central axis O in the side view shown in FIG. 10, and extends to the needle tip 8. The second flat surface 205b is contiguous to the proximal side of the first flat surface 205a in the central axis direction A. The second flat surface 205b is inclined at a predetermined angle larger than the predetermined angle of the first flat surface 205a with respect to the central axis O in the side view shown in FIG. 10. The third flat surface 205c is contiguous to the proximal side of the second flat surface 205b in the central axis direction A. The third flat surface 205c is inclined at a predetermined angle larger than the predetermined angles of the first flat surface 205a and the second flat surface 205b with respect to the central axis O in the side view shown in FIG. 10. The number of flat surfaces constituting the first blade surface portion 205 and the inclination angle are not limited to those in the configuration shown in FIG. 10. The number of flat surfaces constituting the first blade surface portion 205 may be two or four or more.

In the first blade surface portion 205 shown in FIG. 10, a tangent line L3 of the first blade surface portion 205 at a point where the first blade surface portion 205 and the central axis O of the main body 2 intersect with each other also intersects with the second blade surface portion 6 and the third blade surface portion 7 in the side view (see FIG. 10). Here, in a case where the first blade surface portion 205 and the central axis O of the main body 2 intersect with each other at one point on a straight line as shown in FIG. 10, that is, the central axis O of the main body 2 intersects with the flat surface (the second flat surface 205b in the example in FIG. 10) constituting the first blade surface portion 205, an extension of a straight line representing the flat surface is defined as the tangent line L3.

In the second embodiment described above, the concave surface of the first blade surface portion 105 is constituted by a curved surface extending from the proximal end S of the jaw part to the terminal end U, and a flat surface extending from the terminal end U to the needle tip 108. However, the concave surface of the first blade surface portion may be constituted by a curved surface extending from the proximal end S of the jaw part to the needle tip 108.

Further, the puncture needle according to the present disclosure may be configured as shown in FIGS. 11 to 20.

Figure 11A:
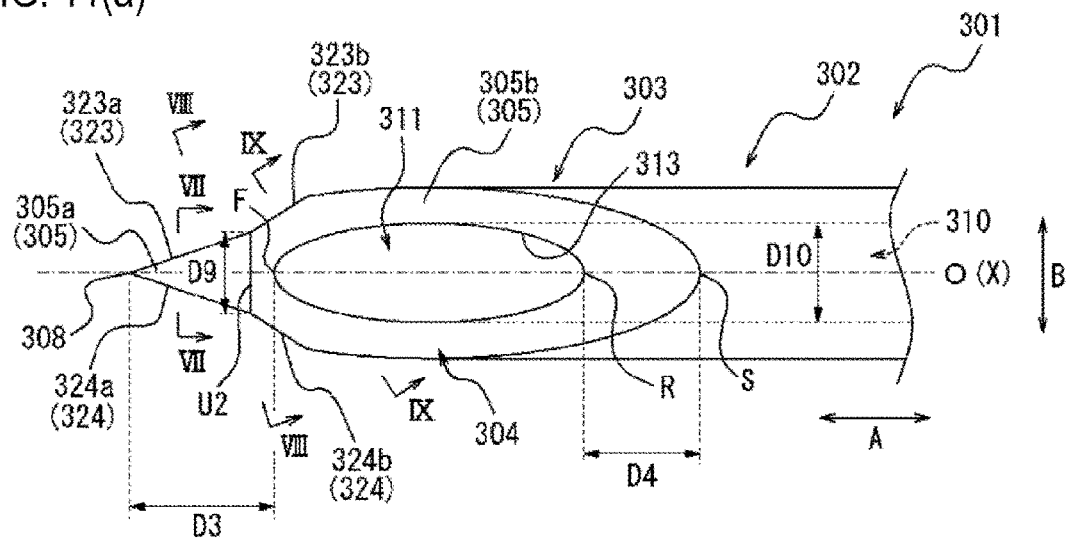
FIGS. 11(a), 11(b), and 11(c) are a front view, a side view, and a rear view of a puncture needle as one embodiment, respectively.
Figure 11B:
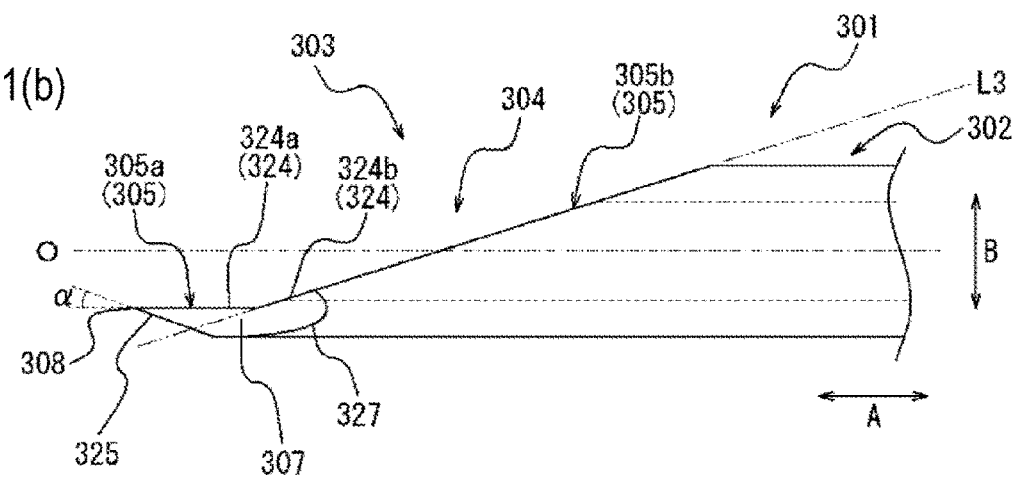
Figure 11C:
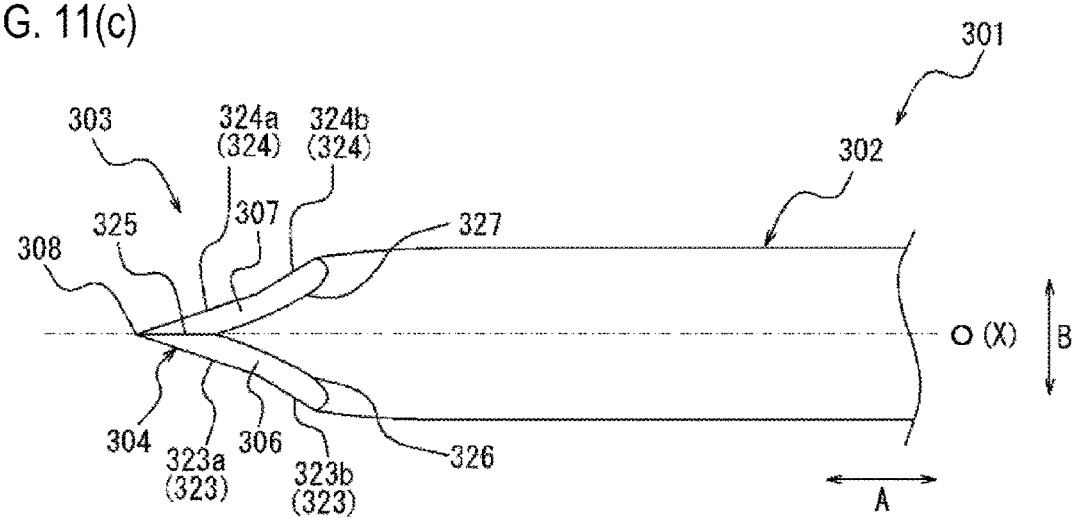
Figure 12:
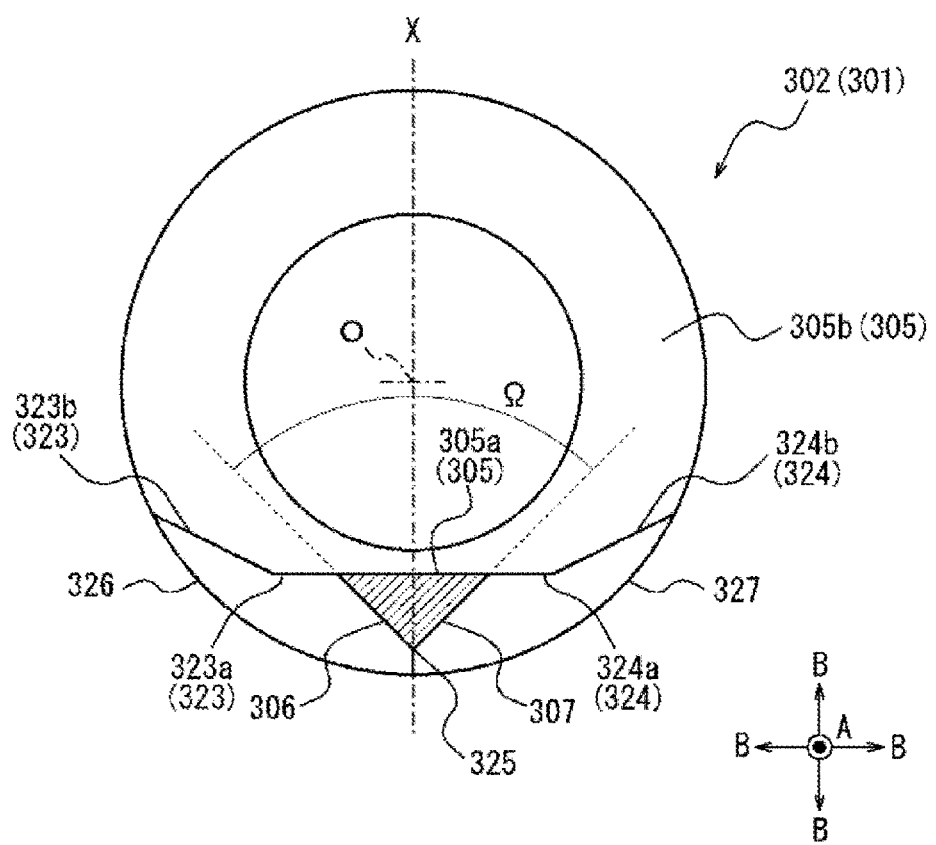
FIG. 12 is a sectional view taken along a line VII-VII in FIG. 11(a).
Figure 13:
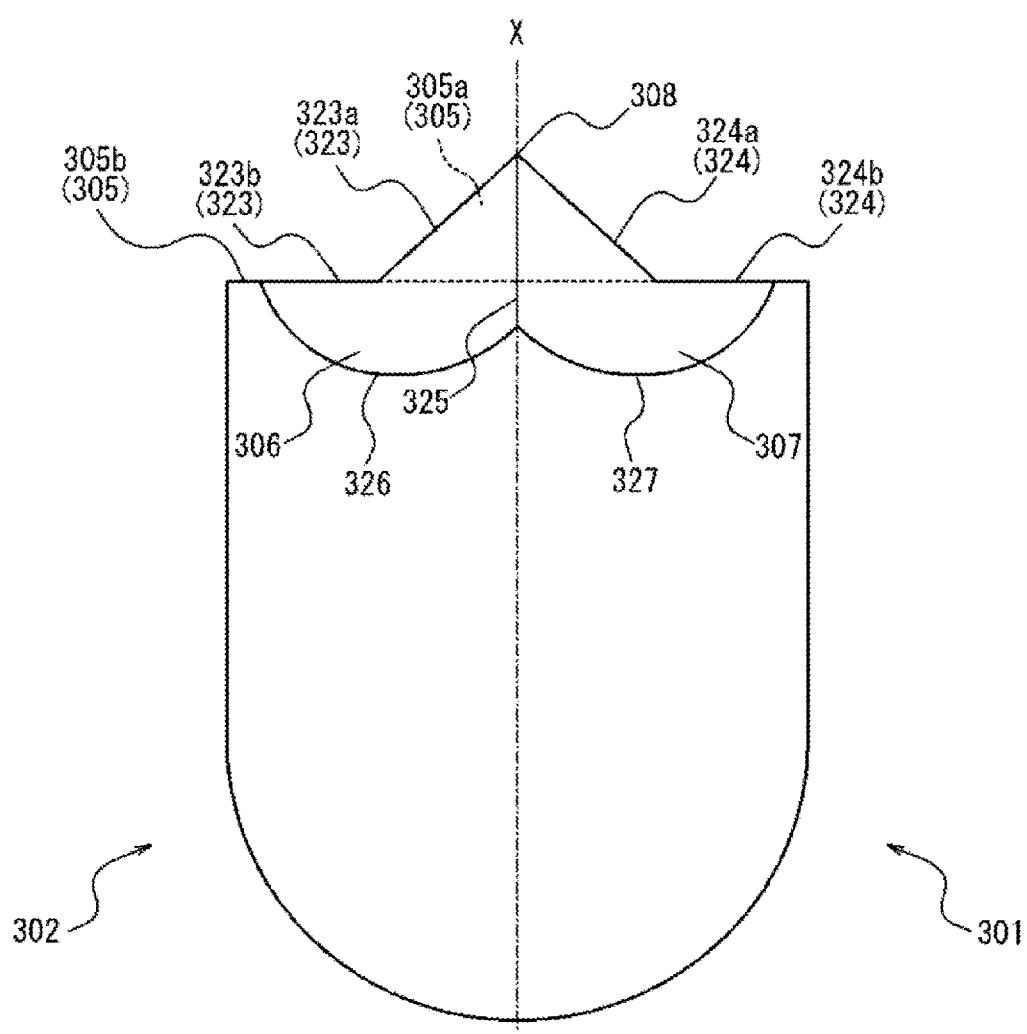
FIG. 13 is a view of a main body viewed from a distal side so that a proximal-side blade surface portion of a first blade surface portion of the puncture needle shown in FIG. 11 appears linear.

FIGS. 11 to 13 are views showing a main body 302 of a puncture needle 301 as one embodiment. Specifically, FIG. 11(a) is a front view of the main body 302 of the puncture needle 301, FIG. 11(b) is a side view of the main body 302 of the puncture needle 301, and FIG. 11(c) is a rear view of the main body 302 of the puncture needle 301. FIG. 12 is a sectional view taken along a line VII-VII in FIG. 11(a). FIG. 13 is a view of the main body 302 viewed from the distal side so that a proximal-side blade surface portion 305b of the first blade surface portion 305 of the puncture needle 301 shown in FIG. 11 appears linear.

As shown in FIGS. 11(a) to 11(c), 12, and 13, the puncture needle 301 has a rod-shaped main body 302, and a blade surface 304 is formed on a distal end portion 303 of the main body 302. Specifically, the main body 302 in the present embodiment is a tubular body, and defines a hollow portion 310 extending in a central axis direction A parallel to a central axis O of the main body 302. More specifically, the main body 302 in the present embodiment is a tubular body in which a cross section thereof perpendicular to the central axis direction A has a substantially circular outer shape.

As shown in FIGS. 11(a) to 11(c), 12, and 13, the blade surface 304 is constituted by a plurality of blade surface portions. Specifically, the blade surface 304 in the present embodiment includes a first blade surface portion 305 as a front blade surface, and a second blade surface portion 306 and a third blade surface portion 307 as back blade surfaces.

In other words, the main body 302 of the puncture needle 301 according to the present embodiment includes the blade surface 304 that is back cut.

The first blade surface portion 305 has a region that extends so as to incline with respect to the central axis O of the main body 302. In addition, the first blade surface portion 305 extends to the needle tip 308. The detail of the first blade surface portion 305 will be described later.

The second blade surface portion 306 and the third blade surface portion 307 are formed on the back side of the first blade surface portion 305. The second blade surface portion 306 forms a first blade edge 323 having the needle tip 308 as one end by a ridge line where the second blade surface portion 306 meets the first blade surface portion 305. The third blade surface portion 307 forms a second blade edge 324 having the needle tip 308 as one end by a ridge line where the third blade surface portion 307 meets the first blade surface portion 305. The second blade surface portion 306 and the third blade surface portion 307 form a third blade edge 325 having the needle tip 308 as one end at the back side of the first blade surface portion 305 by a ridge line where they meet each other. As shown in FIG. 12, each of the second blade surface portion 306 and the third blade surface portion 307 in the present embodiment is constituted by one flat surface inclined with respect to the central plane X. Further, as shown in FIG. 12, the second blade surface portion 306 and the third blade surface portion 307 in the present embodiment have flat surfaces symmetrical with respect to the central plane X.

When the puncture needle 301 punctures the surface of a living body, the first blade edge 323, the second blade edge 324, and the third blade edge 325 function as cutting edges for cutting the skin, and puncture resistance is reduced. The first blade edge 323 and the second blade edge 324 can also be referred to as a first cutting edge and a second cutting edge.

Further, the second blade surface portion 306 forms a fourth blade edge 326 by a ridge line where the second blade surface portion 306 meets the outer peripheral surface of the main body 302. Further, the third blade surface portion 307 forms a fifth blade edge 327 by a ridge line where the third blade surface portion 307 meets the outer peripheral surface of the main body 302.

The first blade surface portion 305 is constituted by a concave surface that is concave in a side view (see FIG. 11(b)) of the main body 302 in which the first blade surface portion 305 appears linear. Further, the concave surface constituting the first blade surface portion 305 in the present embodiment includes a flat surface.

More specifically, the first blade surface portion 305 in the present embodiment includes a distal-side blade surface portion 305a that is flat and that includes the needle tip 308, and a proximal-side blade surface portion 305b that is flat and that is located proximal to the distal-side blade surface portion 305a. The proximal-side blade surface portion 305b is inclined more than the distal-side blade surface portion 305a with respect to the central axis O and the central axis direction A. Further, the proximal-side blade surface portion 305b in the present embodiment is contiguous to the proximal side of the distal-side blade surface portion 305a. Furthermore, the first blade surface portion 305 in the present embodiment is constituted only by the distal-side blade surface portion 305a and the proximal-side blade surface portion 305b described above. As described above, in the present embodiment, the concave surface constituting the first blade surface portion 305 is constituted by the distal-side blade surface portion 305a and the proximal-side blade surface portion 305b.

As shown in FIG. 11(a), an inner edge 313 of the first blade surface portion 305 defines a distal-end opening 311 of the hollow portion 310. The inner edge 313 of the first blade surface portion 305 extends substantially elliptically from a proximal end R in substantially a symmetrical manner with respect to the central plane X and reaches a distal end F of the inner edge 313. A terminal end U2 of the proximal-side blade surface portion 305b of the first blade surface portion 305 is located distal to the distal end F. In a front view seen from the first blade surface portion 305 side, the width D9 (width at the terminal end U2) of the proximal part of the distal-side blade surface portion 305a is smaller than the diameter D10 of the hollow portion 310. The length D3 from the needle tip 308 to the distal end F of the inner edge 313 is longer than the length D4 from the proximal end R of the inner edge 313 of the first blade surface portion 305 to the proximal end S of the jaw part of the first blade surface portion 305.

The first blade surface portion 305 in the present embodiment is constituted by the distal-side blade surface portion 305a and the proximal-side blade surface portion 305b described above as two continuous flat surfaces. However, the first blade surface portion 305 is not limited thereto. The first blade surface portion 305 may be constituted by three or more flat surfaces, as in the first blade surface portion 205 shown in FIG. 10. The distal-side blade surface portion 305a and the proximal-side blade surface portion 305b of the first blade surface portion 305 may not be two flat surfaces that are continuous in the central axis direction A. That is, in a case where the first blade surface portion 305 is constituted by three or more flat surfaces that are continuous in the central axis direction A, the proximal-side blade surface portion 305b may not be a flat surface contiguous to the flat distal-side blade surface portion 305a including the needle tip 308, and may be a flat surface connected to the proximal side of the distal-side blade surface portion 305a with another flat surface (intermediate blade surface portion) therebetween. A ridge line where arbitrary two continuous flat surfaces among multiple flat surfaces constituting the first blade surface portion 305 and having different inclination angles with respect to the central axis O meet each other extends in a direction perpendicular to the central axis direction A. Specifically, in the present embodiment, the ridge line between the distal-side blade surface portion 305a and the proximal-side blade surface portion 305b extends perpendicular to the central axis direction A.

Further, as shown in FIG. 11(b), in the puncture needle 301 in the present embodiment, the distal-side blade surface portion 305a is parallel to the central axis O of the main body 302 and the central axis direction A in the side view of the main body 302 in which the first blade surface portion 305 appears linear. With this configuration, the blade tip angle α can be reduced. Further, as shown in FIG. 11(b), in the puncture needle 301 in the present embodiment, the proximal-side blade surface portion 305b is inclined with respect to the central axis O of the main body 302 and the central axis direction A in the side view of the main body 302 in which the first blade surface portion 305 appears linear.

Moreover, as shown in FIG. 11(b), the distal-side blade surface portion 305a and the proximal-side blade surface portion 305b form an obtuse angle in the side view of the main body 302 in which the first blade surface portion 305 appears linear.

As described above, the first blade surface portion 305 in the present embodiment is constituted by a plurality of flat surfaces. Further, in the first blade surface portion 305 in the present embodiment, a concave surface is formed by a plurality of flat surfaces in the side view (see FIG. 11(b)) of the main body 302 in which the plurality of flat surfaces constituting the first blade surface portion 305 appears linear.

As shown in FIGS. 11(b) and 11(c), the second blade surface portion 306 and the third blade surface portion 307 extend across both the back side of the distal-side blade surface portion 305a and the back side of the proximal-side blade surface portion 305b.

With this configuration, the first blade edge 323 formed by the first blade surface portion 305 and the second blade surface portion 306 has a straight distal-side blade edge 323a and a straight proximal-side blade edge 323b located on the proximal side of the distal-side blade edge 323a. The second blade edge 324 formed by the first blade surface portion 305 and the third blade surface portion 307 also has a straight distal-side blade edge 324a and a straight proximal-side blade edge 324b located on the proximal side of the distal-side blade edge 324a.

The distal-side blade edge 323a of the first blade edge 323 is formed by a ridge line where the distal-side blade surface portion 305a of the first blade surface portion 305 meets the second blade surface portion 306. The proximal-side blade edge 323b of the first blade edge 323 is formed by a ridge line where the proximal-side blade surface portion 305b of the first blade surface portion 305 meets the second blade surface portion 306.

The distal-side blade edge 324a of the second blade edge 324 is formed by a ridge line where the distal-side blade surface portion 305a of the first blade surface portion 305 meets the third blade surface portion 307. The proximal-side blade edge 324b of the second blade edge 324 is formed by a ridge line where the proximal-side blade surface portion 305b of the first blade surface portion 305 meets the third blade surface portion 307.

Here, as shown in FIG. 11(a), the first blade edge 323 has a concave shape in a front view of the main body 302 viewed from the first blade surface portion 305 side. More specifically, as shown in FIG. 11(a), the distal-side blade edge 323a and the proximal-side blade edge 323b of the first blade edge 323 form a concave shape in the front view of the main body 302 viewed from the first blade surface portion 305 side.

Further, as shown in FIG. 11(a), the second blade edge 324 has a concave shape in the front view of the main body 302 viewed from the first blade surface portion 305 side. More specifically, as shown in FIG. 11(a), the distal-side blade edge 324a and the proximal-side blade edge 324b of the second blade edge 324 form a concave shape in the front view of the main body 302 viewed from the first blade surface portion 305 side.

As described above, in the puncture needle 301 in the present embodiment, each of the second blade surface portion 306 and the third blade surface portion 307 extends across both the back side of the distal-side blade surface portion 305a of the first blade surface portion 305 and the back side of the proximal-side blade surface portion 305b of the first blade surface portion 305. As a result, in the puncture needle 301 in the present embodiment, the first blade edge 323 and the second blade edge 324 form a concave shape due to the straight distal-side blade edges 323a and 324a and the straight proximal-side blade edges 323b and 324b, respectively, in the front view (see FIG. 11(a)). Therefore, in the puncture needle 301, the puncture resistance near the needle tip 308 can be reduced by the distal-side blade edge 323a of the first blade edge 323, the distal-side blade edge 324a of the second blade edge 324, and the third blade edge 325. Further, in the puncture needle 301, the skin is easily and largely cut by the proximal-side blade edge 323b of the first blade edge 323 and the proximal-side blade edge 324b of the second blade edge 324. Therefore, the pain experienced by the patient when the cut site is widened during puncture can be reduced.

The first blade edge 323 in the present embodiment is constituted by two straight lines, that is, the distal-side blade edge 323a and the proximal-side blade edge 323b described above. However, the first blade edge 323 is not limited thereto. The first blade edge 323 may be constituted by three or more straight lines. The distal-side blade edge 323a and the proximal-side blade edge 323b of the first blade edge 323 may not be two continuous straight lines. That is, in a case where the first blade edge 323 is constituted by three or more straight lines that extend in different directions, the proximal-side blade edge 323b may not be a straight line connected to the straight distal-side blade edge 323a including the needle tip 308 as one end, and may be a straight line connected to the proximal side of the distal-side blade edge 323a with another straight line (intermediate blade edge) therebetween. Such a modification is similarly applicable to the second blade edge 324.

As shown in FIG. 11(b), in the puncture needle 301 in the present embodiment, the distal-side blade edge 323a of the first blade edge 323 and the distal-side blade edge 324a of the second blade edge 324 are parallel to the central axis O of the main body 302 and the central axis direction A in the side view of the main body 302 in which the first blade surface portion 305 appears linear. With this configuration, the blade tip angle α can be reduced. Further, as shown in FIG. 11(b), in the puncture needle 301 in the present embodiment, the proximal-side blade edge 323b of the first blade edge 323 and the proximal-side blade edge 324b of the second blade edge 324 are inclined with respect to the central axis O of the main body 302 and the central axis direction A in the side view of the main body 302 in which the first blade surface portion 305 appears linear.

Moreover, as shown in FIG. 11(b), the distal-side blade edge 324a and the proximal-side blade edge 324b of the second blade edge 324 form an obtuse angle in the side view of the main body 302 in which the first blade surface portion 305 appears linear. FIG. 11(b) is a side view seen from the third blade surface portion 307 side. In a side view seen from the second blade surface portion 306 side reverse to the side in FIG. 11(b), the distal-side blade edge 323a and the proximal-side blade edge 323b of the first blade edge 323 also have the similar configuration. That is, the distal-side blade edge 323a and the proximal-side blade edge 323b of the first blade edge 323 form an obtuse angle in the side view (side view seen from the side reverse to the side in FIG. 11(b)) of the main body 302 in which the first blade surface portion 305 appears linear.

In addition, when the main body 302 is viewed from the distal side so that the flat blade surface portion (proximal-side blade surface portion 305b in the present embodiment) connected to the proximal side of the distal-side blade surface portion 305a in the first blade surface portion 305 appears linear (see FIG. 13), a part including the needle tip 308 protrudes to one side with respect to the flat blade surface portion (proximal-side blade surface portion 305b in the present embodiment) that appears linear. In other words, in the plan view shown in FIG. 13, the needle tip 308 is located at the vertex that is the intersection of the distal-side blade edge 323a of the first blade edge 323 and the distal-side blade edge 324a of the second blade edge 324, the distal-side blade edge 323a and the distal-side blade edge 324a extending from the flat blade surface portion (proximal-side blade surface portion 305b in the present embodiment) that appears linear. Further, in the plan view shown in FIG. 13, the third blade edge 325 also extends to the needle tip 308. That is, in the plan view shown in FIG. 13, the needle tip 308 is located at the vertex that is the intersection of the distal-side blade edge 323a of the first blade edge 323, the distal-side blade edge 324a of the second blade edge 324, and the third blade edge 325.

Figure 14:
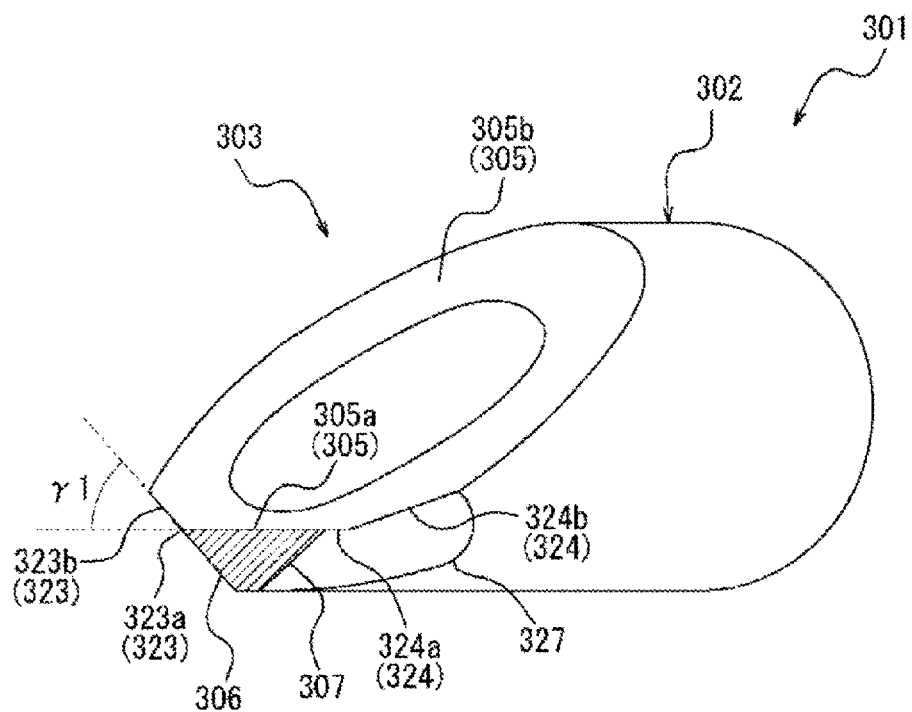
FIG. 14 is a sectional view taken along a line VIII-VIII in FIG. 11(a).
Figure 15:
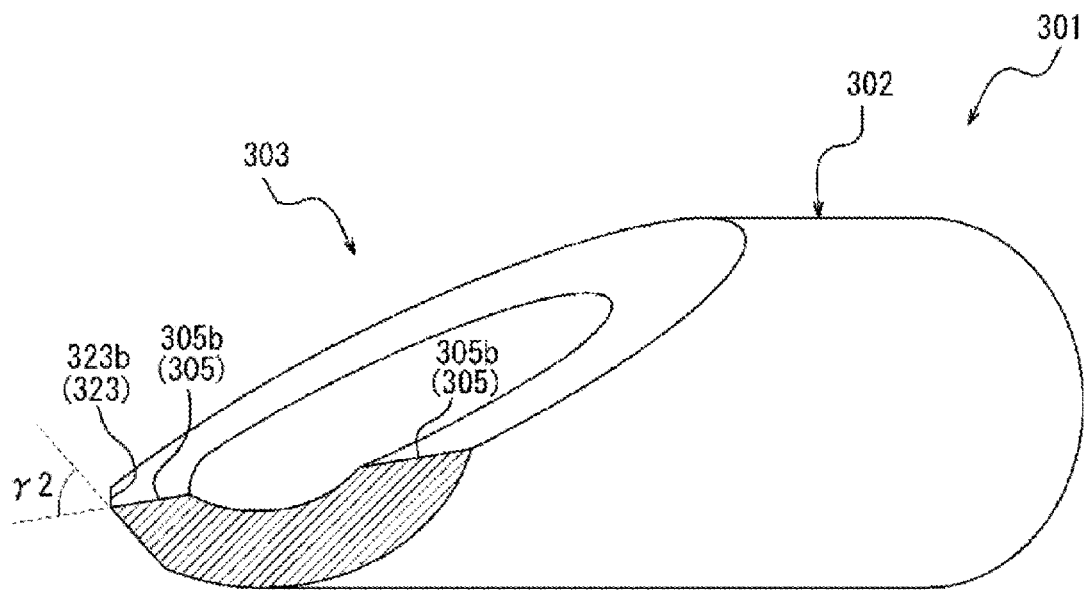
FIG. 15 is a sectional view taken along a line IX-IX in FIG. 11(a).

FIG. 14 is a sectional view taken along a line VIII-VIII in FIG. 11(a). Specifically, FIG. 14 shows a cross section perpendicular to the straight distal-side blade edge 323a of the first blade edge 323. FIG. 15 is a sectional view taken along a line IX-IX in FIG. 11(a). Specifically, FIG. 15 shows a cross section perpendicular to the straight proximal-side blade edge 323b of the first blade edge 323.

In FIG. 14, in a cross section perpendicular to the distal-side blade edge 323a of the first blade edge 323, the angle between the distal-side blade surface portion 305a of the first blade surface portion 305 and the second blade surface portion 306 is referred to as a "first angle γ1". In FIG. 15, in a cross section perpendicular to the proximal-side blade edge 323b of the first blade edge 323, the angle between the proximal-side blade surface portion 305b of the first blade surface portion 305 and the second blade surface portion 306 is referred to as a "second angle γ2". As shown in FIGS. 14 and 15, both the first angle γ1 and the second angle γ2 are acute. Further, the first angle γ1 is smaller than the second angle γ2.

While FIGS. 14 and 15 show only the magnitude relation between the first angle γ1 at the position of the distal-side blade edge 323a of the first blade edge 323 and the second angle γ2 at the position of the proximal-side blade edge 323b of the first blade edge 323, the similar magnitude relation is established by comparing similar angles for the second blade edge 324.

Further, as shown in FIG. 11(b), a tangent line L3 of the first blade surface portion 305 at a point where the first blade surface portion 305 and the central axis of the main body 302 intersect with each other intersects with the third blade surface portion 307 in the side view of the main body 302 in which the first blade surface portion 305 appears linear. FIG. 11(b) shows the side viewed from the third blade surface portion 307 side, but the same applies to the side viewed from the second blade surface portion 306 side. That is, in a side view seen from the side opposite to the side in FIG. 11(b), the tangent line L3 intersects with the second blade surface portion 306.

Next, an overview and results of a puncture resistance test performed using two examples of the puncture needle will be described. The two examples are one example of the puncture needle 101 shown in FIGS. 6 and 7 (hereinafter, referred to as "Example 1") and one example of the puncture needle 301 shown in FIGS. 11 to 15 (hereinafter, referred to as "Example 2"). The blade tip angles α in Examples 1 and 2 are 20 degrees (see FIGS. 6(b) and 11(b)). The sectional angle Ω of Example 1 is 60 degrees (see FIG. 7). Further, the sectional angle Ω of Example 2 is 75 degrees (see FIG. 12). Furthermore, the inclination angle of the proximal-side blade surface portion 305b of the first blade surface portion 305 with respect to the central axis direction A in Example 2 is 16.6 degrees. The blade surface length is the same between Example 1 and Example 2. Specifically, the blade surface length is 1.7 mm.

In this puncture resistance test, five test pieces are prepared for each of the two types of puncture needles in Example 1 and Example 2 described above, and puncture resistances of 10 puncture needles in total are measured. In the puncture resistance test, each puncture needle is inserted into a silicone sheet having a thickness of 0.5 mm, and the puncture resistance is measured. The silicone sheet used in this test is a silicon rubber sheet manufactured by Tigers Polymer Corporation. The puncture angle of the puncture needle to the silicone sheet is 30 degrees. In this test, the measured parameters are the puncture resistance value [gf] when the needle tip of each puncture needle passes through the silicone sheet, and the puncture resistance value [gf] when the proximal end of a jaw part (heel of the jaw part) of the blade surface portion of each puncture needle passes through the silicone sheet. Other various conditions in this test are similar to those of the abovementioned puncture resistance test whose results are shown in Table 1, and thus will not be repeated here.

Table 3 below shows the results of the puncture resistance test.

TABLE 3

|  | Example 1 | | Example 2 | |
| --- | --- | --- | --- | --- |
|  | Needle tip | Proximal end of jaw part | Needle tip | Proximal end of jaw part |
| Average [gf] | 13.9 | 25.9 | 9.2 | 18.5 |
| Maximum [gf] | 16.7 | 30.5 | 10.8 | 25.8 |
| Minimum [gf] | 12.2 | 21.5 | 8.0 | 13.1 |
| Standard deviation | 1.9 | 3.8 | 1.0 | 4.9 |
| First test piece | 14.7 | 30.5 | 8.9 | 25.8 |
| Second test piece | 12.3 | 26.0 | 10.8 | 16.4 |
| Third test piece | 16.7 | 28.7 | 9.0 | 16.2 |
| Fourth test piece | 12.1 | 22.8 | 9.3 | 13.1 |
| Fifth test piece | 13.7 | 21.5 | 8.0 | 20.9 |

It can be seen from Table 3 that, according to the puncture needles in Example 1 and Example 2, the puncture resistance at the needle tip and the puncture resistance at the proximal end of the jaw part can be both reduced. Further, as shown in Table 3, the puncture needle in Example 2 can provide smaller puncture resistance at the needle tip and smaller puncture resistance at the proximal end of the jaw part than the puncture needle in Example 1. In particular, the puncture needle in Example 2 can provide a greater effect of reducing the puncture resistance at the proximal end of the jaw part than the puncture needle in Example 1. The reason for this is that, in the puncture needle in Example 2, the inclination angle at the proximal end of the jaw part of the first blade surface portion with respect to the central axis direction can be reduced, as compared with the puncture needle in Example 1. Therefore, regarding the puncture resistance at the proximal end of the jaw part of the first blade surface portion, the puncture needle 301 shown in FIGS. 11 to 15 is more preferable than the puncture needle 101 shown in FIGS. 6 and 7.

Next, a catheter set 500 and a catheter assembly 500a, as one embodiment, obtained by assembling the catheter set 500 will be described with reference to FIGS. 16 to 20.

Figure 16A:
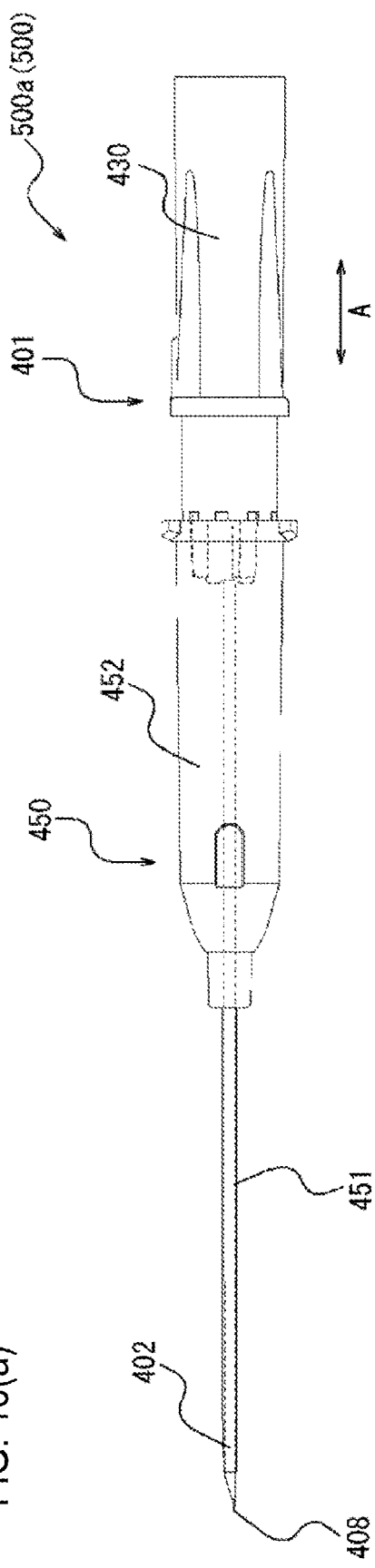
FIGS. 16(a) and 16(b) are an external view and a sectional view of a catheter assembly as one embodiment, respectively.
Figure 16B:
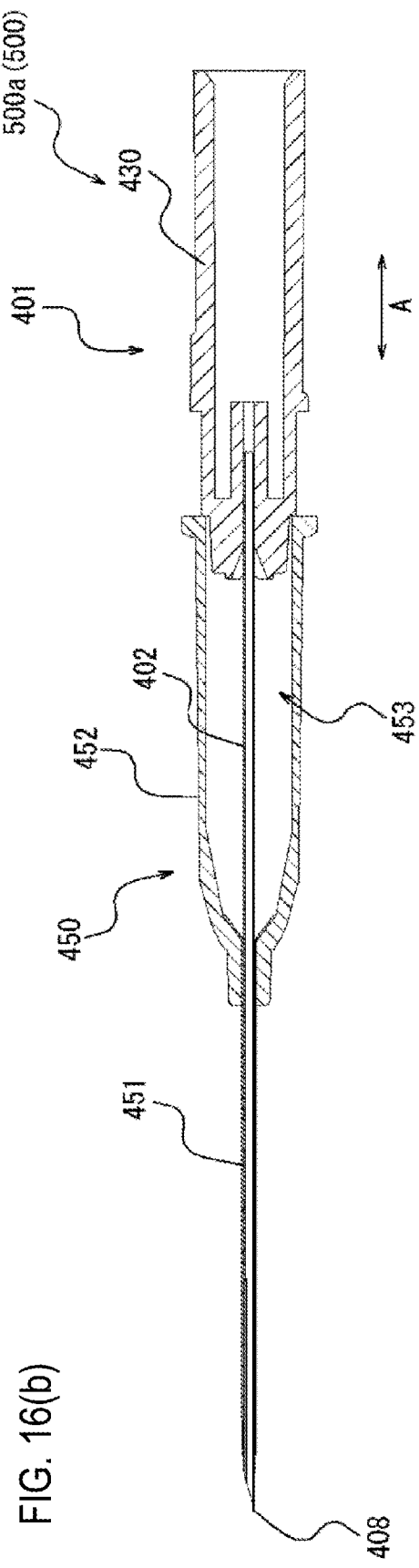

FIGS. 16(a) and 16(b) are an external view and a sectional view of the catheter assembly 500a, respectively. As shown in FIGS. 16(a) and 16(b), the catheter assembly 500a includes a puncture needle 401 as an inner tube member, and an outer tube member 450. Here, a configuration including the puncture needle 401 and the outer tube member 450 is referred to as a "catheter set 500". A state where the puncture needle 401 and the outer tube member 450 in the catheter set 500 are assembled together is referred to as a "catheter assembly 500a".

As shown in FIGS. 16(a) and 16(b), the puncture needle 401 includes a main body 402 and a needle hub 430 as a needle hub.

As shown in FIGS. 16(a) and 16(b), the outer tube member 450 includes a catheter 451 through which the puncture needle 401 is inserted, and a catheter hub 452 holding the catheter 451. More specifically, the main body 402 of the puncture needle 401 is inserted through the catheter 451.

Figure 19A:
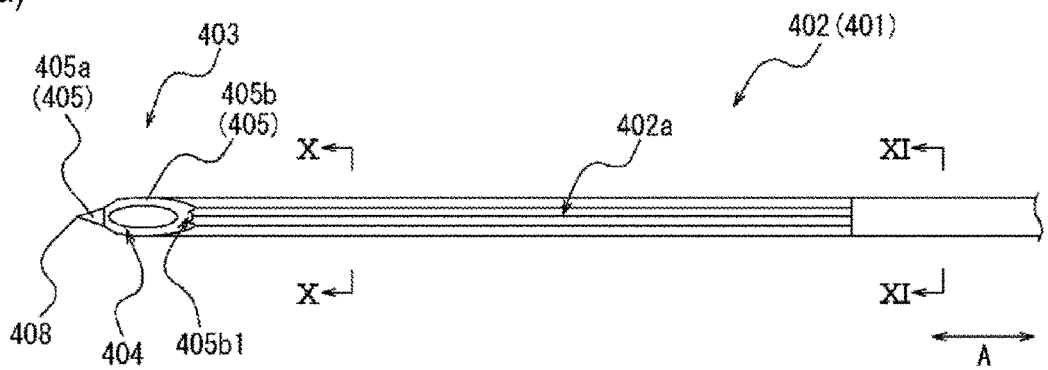
FIG. 19(a) is an enlarged view of a part of a main body of the puncture needle shown in FIG. 18(a), and FIGS. 19(b) and 19(c) are sectional views along a line X-X and along a line XI-XI in FIG. 19(a), respectively.
Figure 19B:
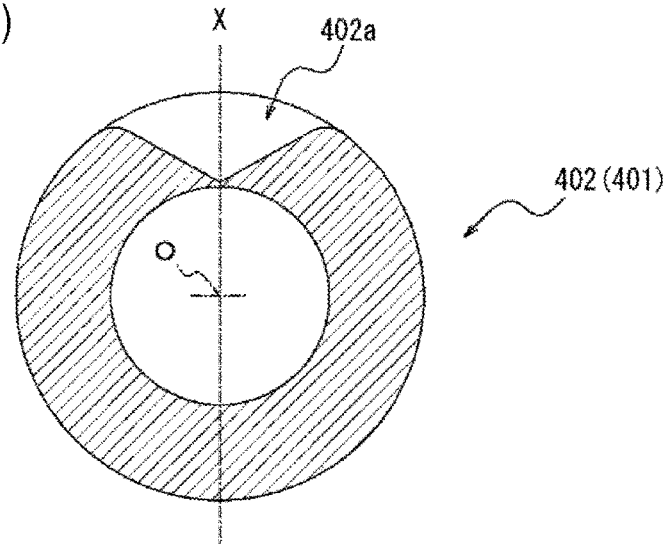
Figure 19C:
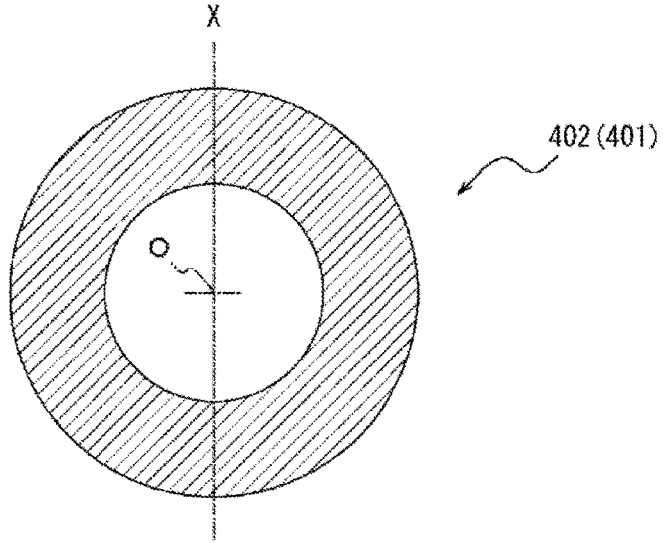

FIGS. 17(a) and 17(b) are an external view and a sectional view of the outer tube member 450, respectively. FIGS. 18(a) and 18(b) are an external view and a sectional view of the puncture needle 401, respectively. FIG. 19(a) is an enlarged view showing a part of the main body 402 of the puncture needle 401 shown in FIG. 18(a). FIGS. 19(b) and 19(c) are a sectional view taken along a line X-X and a sectional view taken along a line XI-XI in FIG. 19(a), respectively.

As shown in FIG. 17, the catheter hub 452 of the outer tube member 450 holds a proximal end portion of the catheter 451. A receiving opening 453 for receiving the puncture needle 401 is formed at the proximal end of the catheter hub 452. The main body 402 of the puncture needle 401 is inserted into the catheter 451 through the receiving opening 453 of the catheter hub 452. The puncture needle 401 is inserted into the catheter 451 until the needle tip 408 of the main body 402 projects beyond the distal end of the catheter 451.

As shown in FIG. 18, the puncture needle 401 includes the main body 402 having a blade surface 404 formed at a distal end portion 403, and a needle hub 430 holding a proximal end portion of the main body 402. When the main body 402 of the puncture needle 401 is inserted into the catheter 451 through the receiving opening 453 of the catheter hub 452 of the outer tube member 450, the distal end portion of the needle hub 430 is also inserted into the receiving opening 453 of the catheter hub 452. When the needle tip 408 of the main body 402 of the puncture needle 401 is inserted to a predetermined position protruding from the distal end of the catheter 451, the needle hub 430 is locked by the catheter hub 452. Thus, the puncture needle 401 and the outer tube member 450 are assembled together and integrated to form the catheter assembly 500a as shown in FIG. 16.

As shown in FIG. 19, the blade surface 404 is formed on the distal end portion 403 of the main body 402 of the puncture needle 401. Similar to the blade surface 304 shown in FIG. 11, the blade surface 404 includes a first blade surface portion 405, a second blade surface portion, and a third blade surface portion. The shapes of the second blade surface portion and the third blade surface portion of the blade surface 404 are the same as the shapes of the second blade surface portion 306 and the third blade surface portion 307 shown in FIG. 11. The shape of a distal-side blade surface portion 405a of the first blade surface portion 405 is the same as the shape of the distal-side blade surface portion 305a of the first blade surface portion 305 shown in FIG. 11. The shape of a proximal-side blade surface portion 405b of the first blade surface portion 405 is different from the shape of the proximal-side blade surface portion 305b of the first blade surface portion 305 shown in FIG. 11. A notch 405b1 is defined by a groove 402a formed in the outer peripheral surface of the main body 402 in a jaw part of the proximal-side blade surface portion 405b of the first blade surface portion 405. Except for this point, the proximal-side blade surface portion 405b of the first blade surface portion 405 is similar to the proximal-side blade surface portion 305b shown in FIG. 11.

The first blade surface portion 405 of the blade surface 404 of the puncture needle 401 may have a curved surface as shown in FIGS. 1 and 6. Further, the first blade surface portion 405 of the blade surface 404 of the puncture needle 401 may have three or more flat surfaces having different inclination angles as shown in FIG. 10.

The puncture needle 401 of the catheter assembly 500a includes a notification portion capable of providing notification about blood backflow to the outside. As described above, the groove 402a extending in the central axis direction A is formed in the outer peripheral surface of the main body 402 of the puncture needle 401. The notification portion of the puncture needle 401 is constituted by the groove 402a. As shown in FIG. 19, the groove 402a extends from the notch 405b1 of the blade surface 404 toward the proximal side in the central axis direction A, and terminates at a predetermined position of the main body 402. The groove 402a is set to have a length and a position such that, in an assembled state of the outer tube member 450 and the puncture needle 401, the groove 402a starts from a position distal to the most distal end of the catheter 451 and terminates at a position proximal to the most distal end of the catheter 451. Therefore, when the distal end portion 403 of the puncture needle 401 is inserted into a blood vessel, blood backflow can be visually recognized from outside using the groove 402a. That is, blood flows into the space between the inner surface of the catheter 451 and the outer surface of the main body 402 of the puncture needle 401 due to the groove 402a. Since the catheter 451 is transparent or semi-transparent, the inflowing blood can be viewed through the outer surface of the catheter. Thus, blood backflow (flashback) can be visually recognized.

Figure 20:
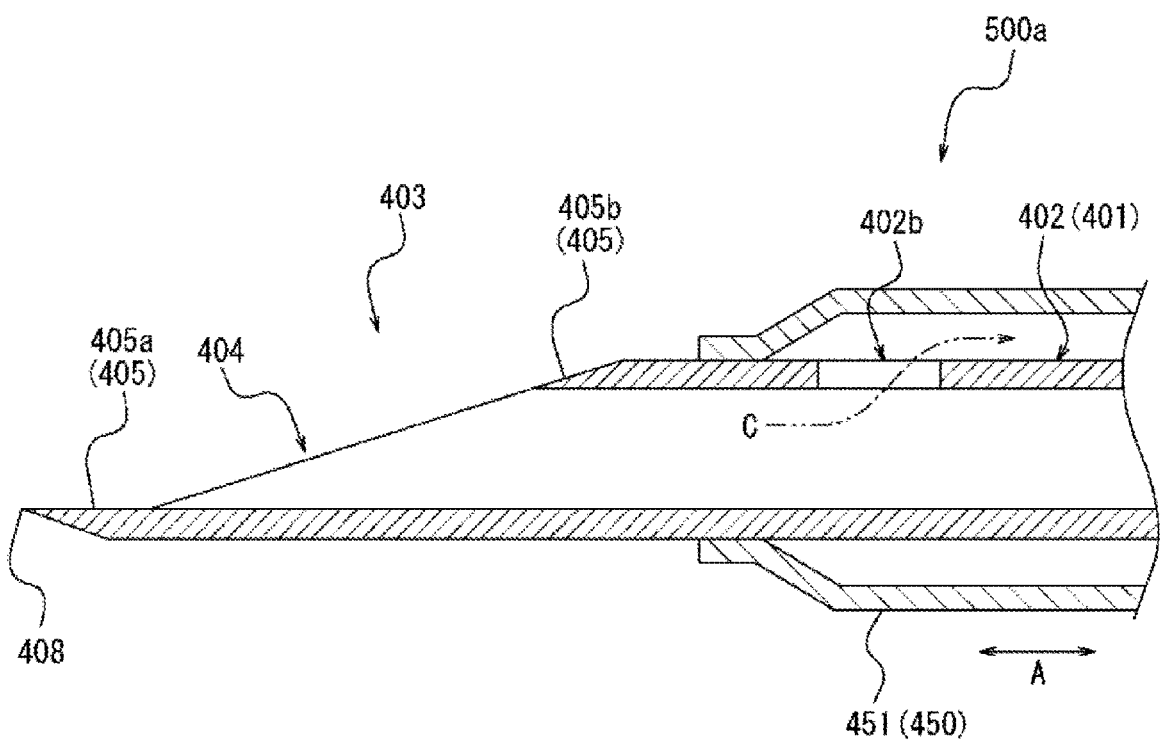
FIG. 20 is a view showing a modification of a notification portion of the puncture needle shown in FIG. 19.

The notification portion of the puncture needle 401 is not limited to the groove 402a described above. FIG. 20 is a view showing a modification of the notification portion shown in FIG. 19. The notification portion of the puncture needle 401 shown in FIG. 20 is constituted by a side hole 402b. Blood flowing backward flows from the inside of the main body 402 of the puncture needle 401 to a space between the inner surface of the catheter 451 and the outer surface of the main body 402 of the puncture needle 401 via the side hole 402b as indicated by an arrow C. Thus, the blood backflow can be visually recognized from the outside of the catheter. Further, the notification portion of the puncture needle 401 may have a configuration other than the abovementioned groove 402a (see FIG. 19) and the side hole 402b (see FIG. 20) as long as it can provide notification about the blood backflow to the outside.

The catheter assembly according to the present disclosure is not limited to have the specific configuration indicated in the above embodiments, and various modifications and changes are possible without departing from the scope of the claims. For example, although the needle hub 430 and the catheter hub 452 of the abovementioned catheter assembly 500a have a substantially columnar outer shape, they may have an outer shape of a polygonal column.

Figure 22:
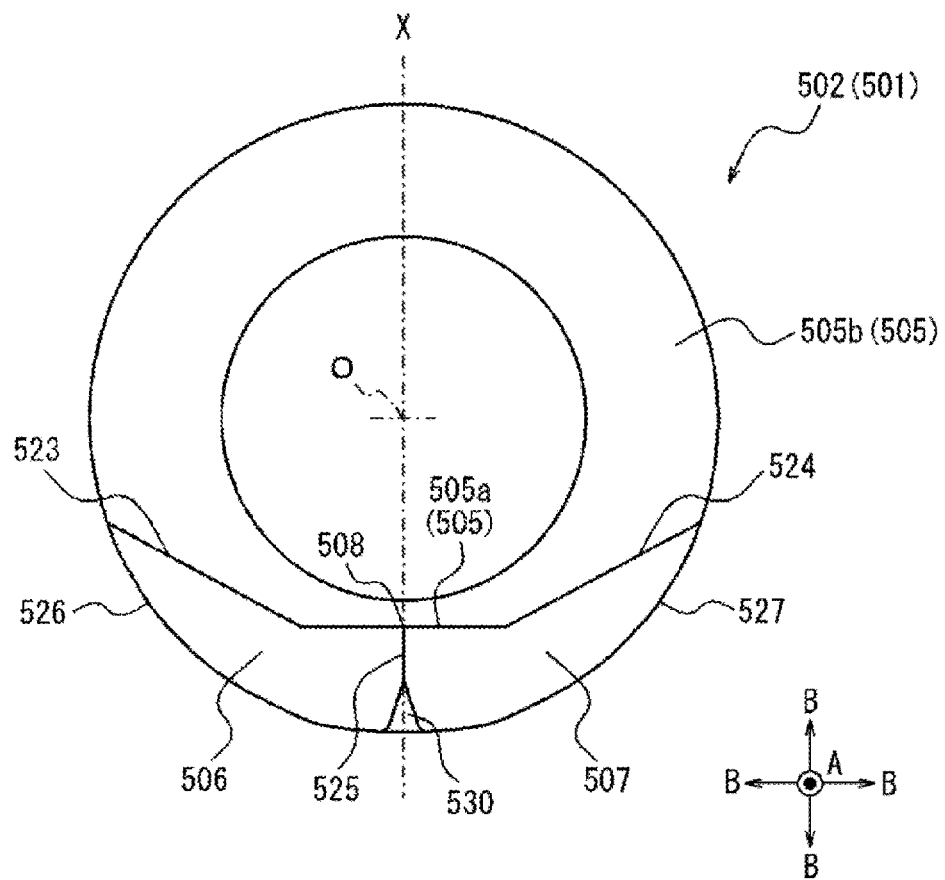
FIG. 22 is a view of the main body of the puncture needle shown in FIG. 21 as viewed from a distal side in a central axis direction.

FIG. 21 is a view showing a main body 502 of a puncture needle 501 as one embodiment of the puncture needle according to the present disclosure. Specifically, FIG. 21(a)

is a front view of the main body 502 of the puncture needle 501, FIG. 21(b) is a side view of the main body 502 of the puncture needle 501, and FIG. 21(c) is a rear view of the main body 502 of the puncture needle 501. FIG. 22 is a view of the main body 502 of the puncture needle 501 as viewed from a distal side in a central axis direction.

As shown in FIGS. 21(a) to 21(c), and 22, the puncture needle 501 has a rod-shaped main body 502, and a blade surface 504 is formed on a distal end portion 503 of the main body 502. Specifically, the main body 502 in the present embodiment is a tubular body, and defines a hollow portion 510 extending in a central axis direction A parallel to a central axis O of the main body 502. More specifically, the main body 502 in the present embodiment is a tubular body in which a cross section thereof perpendicular to the central axis direction A has a substantially circular outer shape.

As shown in FIGS. 21(a) to 21(c), and 22, the blade surface 504 is constituted by a plurality of blade surface portions. Specifically, the blade surface 504 in the present embodiment includes a first blade surface portion 505 as a front blade surface, and a second blade surface portion 506 and a third blade surface portion 507 as back blade surfaces. In other words, the main body 502 of the puncture needle 501 according to the present embodiment includes the blade surface 504 that is back cut.

The first blade surface portion 505 has a region that extends so as to incline with respect to the central axis O of the main body 502. Further, the first blade surface portion 505 extends to the needle tip 508. The first blade surface portion 505 in the present embodiment includes a distal-side blade surface portion 505a that is flat and that includes the needle tip 508, and a proximal-side blade surface portion 505b that is flat and that is located proximal to the distal-side blade surface portion 505a.

The second blade surface portion 506 and the third blade surface portion 507 are formed on the back side of the first blade surface portion 505. The second blade surface portion 506 forms a first blade edge 523 having the needle tip 508 as one end by a ridge line where the second blade surface portion 506 meets the first blade surface portion 505. The third blade surface portion 507 forms a second blade edge 524 having the needle tip 508 as one end by a ridge line where the third blade surface portion 507 meets the first blade surface portion 505. The second blade surface portion 506 and the third blade surface portion 507 form a third blade edge 525 having the needle tip 508 as one end at the back side of the first blade surface portion 505 by a ridge line where they meet each other.

As shown in FIG. 22, each of the second blade surface portion 506 and the third blade surface portion 507 in the present embodiment is constituted by a single flat surface inclined with respect to the central plane X. Further, as shown in FIG. 22, the second blade surface portion 506 and the third blade surface portion 507 in the present embodiment have flat surfaces symmetrical with respect to the central plane X.

Further, the second blade surface portion 506 forms a fourth blade edge 526 by a ridge line where the second blade surface portion 506 meets an outer peripheral surface 502a of the main body 502. Further, the third blade surface portion 507 forms a fifth blade edge 527 by a ridge line where the third blade surface portion 507 meets the outer peripheral surface 502a of the main body 502.

Here, comparing the puncture needle 501 according to the present embodiment and the puncture needle 301 (see FIG. 11, etc.), the puncture needle 501 is different from the puncture needle 301 in having a transition portion 530 on the back side of the first blade surface portion 505, and is the same in other configurations. Therefore, the transition portion 530 will be described below in detail, and the description of the configurations of the puncture needle 501 same as those of the puncture needle 301 (see FIG. 11, etc.) will be omitted.

As shown in FIG. 21(b), the transition portion 530 is formed on the proximal side of the third blade edge 525 and on the distal side of the outer peripheral surface 502a of the main body 502. The transition portion 530 continuously extends from the straight third blade edge 525 to the proximal side. The transition portion 530 is curved to protrude outward in the radial direction in a side view (see FIG. 21(b)). The proximal side of the transition portion 530 is continuous with the outer peripheral surface 502a of the main body 502. In the central axis direction A of the main body 502, the proximal end of the transition portion 530 is located at the same position as or distal to the terminal end U2 of the proximal-side blade surface portion 505b of the first blade surface portion 505.

As shown in FIG. 21(c), the transition portion 530 is a surface formed between the fourth blade edge 526 and the fifth blade edge 527. More specifically, the transition portion 530 is a curved surface formed between the fourth blade edge 526 and the fifth blade edge 527. The transition portion 530 has a shape of an isosceles triangle in a rear view (see FIG. 21(c)).

As shown in FIG. 22, the transition portion 530 is contiguous to the proximal end of the third blade edge 525. Due to the configuration in which the transition portion 530 is formed, during puncture of the puncture needle 501 into a blood vessel, the contact resistance to the posterior wall of the blood vessel is reduced, and the influence on the blood vessel is suppressed.

INDUSTRIAL APPLICABILITY

The present disclosure relates to a puncture needle.

REFERENCE SIGNS LIST 1, 101, 201, 301, 401, 501 Puncture needle
2, 102, 302, 402, 502 Main body
3, 103, 303, 403, 503 Distal end portion
4, 104, 304, 404, 504 Blade surface
5, 105, 205, 305, 405, 505 First blade surface portion
6, 106, 306, 506 Second blade surface portion
7, 107, 307, 507 Third blade surface portion
8, 108, 308, 408, 508 Needle tip
10, 110, 310, 510 Hollow portion
11, 111, 311 Distal-end opening
13, 113, 313 Inner edge of first blade surface portion
14 Outer edge of first blade surface portion
15 Proximal-side outer edge portion
23, 123, 323, 523 First blade edge
24, 124, 324, 524 Second blade edge
25, 125, 325, 525 Third blade edge
26, 126, 326, 526 Fourth blade edge
27, 127, 327, 527 Fifth blade edge
105a Jaw part of first blade surface portion
205a First flat surface
205b Second flat surface
205c Third flat surface
305a, 405a, 505a Distal-side blade surface portion
305b, 405b, 505b Proximal-side blade surface portion
323a Distal-side blade edge of first blade edge
323b Proximal-side blade edge of first blade edge 324a Distal-side blade edge of second blade edge
324b Proximal-side blade edge of second blade edge
402a Groove
402b Side hole
405b1 Notch
430 Needle hub
450 Outer tube member
451 Catheter
452 Catheter hub
453 Receiving opening
500 Catheter set
500a Catheter assembly
502a Outer peripheral surface of main body
A Central axis direction of main body
B Radial direction of main body
C Flow of blood flowing backward
F Distal end of inner edge of first blade surface portion
H Blade surface length
L1 Straight line passing through proximal end of first blade surface portion and needle tip in side view
L2 Tangent line of first blade surface portion at position of needle tip in side view
L3 Tangent line of first blade surface portion at point where first blade surface portion and central axis of main body intersect with each other in side view
L4 Tangent line of inner edge of first blade surface portion in distal-end view
D1 Length from needle tip to terminal end of concave curved surface of first blade surface portion
D2 Length from terminal end of concave curved surface of first blade surface portion to distal end of inner edge
D3 Length from needle tip to distal end of inner edge
D4 Length from proximal end of inner edge of first blade surface portion to proximal end of jaw part of first blade surface portion
D5 Length of third blade edge in central axis direction in rear view
D9 Width of proximal part of distal-side blade surface portion
D10 Diameter of hollow portion
M Midpoint of blade surface region in central axis direction A
N Thickness of peripheral wall of main body
O Central axis
P Proximal end of first blade edge
Q Proximal end of second blade edge
R Proximal end of inner edge of first blade surface portion
S Proximal end of jaw part of first blade surface portion
T Blade surface region
U Terminal end of concave curved surface of first blade surface portion
U2 Terminal end of proximal-side blade surface portion of first blade surface portion
V1 Width between first blade edge and fourth blade edge in rear view
V2 Width between second blade edge and fifth blade edge in rear view
W Width of cutting edge
X Central plane
Y1 Point on first blade edge, point on second blade edge
Y2 Point on inner edge of first blade surface portion
Ω Sectional angle between second blade surface portion and third blade surface portion
α Blade tip angle
β Distal end angle
γ1 First angle
γ2 Second angle
δ Angle between third blade edge and central axis in side view
θ1 Angle between first blade surface portion and central plane in cross section perpendicular to central axis direction
θ2 Angle between second blade surface portion and central plane in cross section perpendicular to central axis direction
θ3 Angle between third blade surface portion and central plane in cross section perpendicular to central axis direction

The invention claimed is:

1. A puncture needle for medical use, the puncture needle comprising:
a main body that is rod-shaped and that comprises a distal end portion comprising a blade surface,
wherein the blade surface comprises:
a first blade surface portion that extends so as to incline with respect to a central axis of the main body, and
a second blade surface portion that is formed on a back side of the first blade surface portion,
wherein a blade edge having a needle tip at one end is formed by a ridge line where the first blade surface portion meets the second blade surface portion,
wherein the first blade surface portion is constituted by a concave surface that is concave in a side view of the main body, and
wherein the blade edge forms a concave shape in a front view of the main body as seen from a first blade surface portion side.

2. The puncture needle according to claim 1,
wherein the concave surface constituting the first blade surface portion comprises a concave curved surface.

3. The puncture needle according to claim 1,
wherein the concave surface constituting the first blade surface portion comprises a flat surface.

4. The puncture needle according to claim 1,
wherein the second blade surface portion extends to a proximal side beyond a midpoint of a blade surface region where the blade surface is formed in a central axis direction.

5. The puncture needle according to claim 1,
wherein, in the side view, a tangent line of the first blade surface portion at a position of the needle tip extends substantially parallel to the central axis of the main body.

6. A catheter assembly comprising:
the puncture needle according to claim 1;
a catheter into which the puncture needle is inserted; and
a catheter hub holding the catheter.

7. A puncture needle for medical use, the puncture needle comprising:
a main body that comprises a distal end portion comprising a blade surface,
wherein the blade surface comprises:
a first blade surface portion having at least a region that extends so as to incline with respect to a central axis of the main body, and
a second blade surface portion that is formed on a back side of the first blade surface portion,
wherein a blade edge having a needle tip at one end is formed by a ridge line where the first blade surface portion meets the second blade surface portion,
wherein the blade edge has a distal-side blade edge that is straight and a proximal-side blade edge that is straight and located proximal of the distal-side blade edge, and wherein, in a front view of the main body as seen from a first blade surface portion side, the distal-side blade edge and the proximal-side blade edge form a concave shape.

8. The puncture needle according to claim 7, wherein the distal-side blade edge and the proximal-side blade edge form an obtuse angle in a side view of the main body.

9. The puncture needle according to claim 7, wherein the distal-side blade edge is parallel to the central axis of the main body in a side view of the main body.

10. A puncture needle for medical use, the puncture needle comprising:
a main body that comprises a distal end portion comprising a blade surface,
wherein the blade surface comprises:
a first blade surface portion having at least a region that extends so as to incline with respect to a central axis of the main body, and
a second blade surface portion that is formed on a back side of the first blade surface portion,
wherein a blade edge having a needle tip at one end is formed by a ridge line where the first blade surface portion meets the second blade surface portion,
wherein the first blade surface portion comprises a distal-side blade surface portion that is flat and that includes the needle tip, and a proximal-side blade surface portion that is flat, is inclined more than the distal-side blade surface portion with respect to the central axis, and is located proximal of the distal-side blade surface portion, and
wherein the second blade surface portion extends across both a back side of the distal-side blade surface portion and a back side of the proximal-side blade surface portion.

11. The puncture needle according to claim 10,
wherein the blade edge comprises a distal-side blade edge that is straight and is formed by a ridge line where the distal-side blade surface portion of the first blade surface portion meets the second blade surface portion, and a proximal-side blade edge that is straight and is formed by a ridge line where the proximal-side blade surface portion of the first blade surface portion meets the second blade surface portion, and
wherein the distal-side blade edge and the proximal-side blade edge form a concave shape in a front view of the main body as viewed from a first blade surface portion side.

12. The puncture needle according to claim 10, wherein the distal-side blade surface portion is parallel to the central axis of the main body in a side view of the main body.

13. The puncture needle according to claim 10, wherein the distal-side blade surface portion and the proximal-side blade surface portion form an obtuse angle in a side view of the main body.

14. The puncture needle according to claim 10,
wherein the blade surface comprises a third blade surface portion that is formed on a back side of the first blade surface portion,
wherein a second blade edge having the needle tip at one end is formed by a ridge line where the first blade surface portion meets the third blade surface portion,
wherein the second blade surface portion and the third blade surface portion form a third blade edge having the needle tip as one end by a ridge line where the second blade surface portion meets the third blade surface portion on the back side of the first blade surface portion, and
a transition portion is formed on a proximal side of the third blade edge and on a distal side of an outer peripheral surface of the main body.

15. A puncture needle for medical use, the puncture needle comprising:
a main body that comprises a distal end portion comprising a blade surface,
wherein the blade surface comprises:
a first blade surface portion having at least a region that extends so as to incline with respect to a central axis of the main body, and
a second blade surface portion that is formed on a back side of the first blade surface portion,
wherein a blade edge having a needle tip at one end is formed by a ridge line where the first blade surface portion meets the second blade surface portion,
wherein the first blade surface portion comprises a distal-side blade surface portion that is flat and that includes the needle tip, and a proximal-side blade surface portion that is flat, is inclined more than the distal-side blade surface portion with respect to the central axis, and is located proximal of the distal-side blade surface portion,
wherein the blade edge comprises a distal-side blade edge that is straight and is formed by a ridge line where the distal-side blade surface portion of the first blade surface portion meets the second blade surface portion, and a proximal-side blade edge that is straight and is formed by a ridge line where the proximal-side blade surface portion of the first blade surface portion meets the second blade surface portion, and
wherein the distal-side blade edge and the proximal-side blade edge form a concave shape in a front view when the main body is viewed from a first blade surface portion side.

16. The puncture needle according to claim 15, comprising,
wherein the blade surface comprises a third blade surface portion that is formed on a back side of the first blade surface portion,
wherein a second blade edge having the needle tip at one end is formed by a ridge line where the first blade surface portion meets the third blade surface portion,
wherein the second blade surface portion and the third blade surface portion form a third blade edge having the needle tip as one end by a ridge line where the second blade surface portion meets the third blade surface portion on the back side of the first blade surface portion, and
a curved transition portion is formed on a proximal side of the third blade edge and on a distal side of an outer peripheral surface of the main body.

\* \* \* \* \*